United States Patent [19]

Nagano et al.

[11] Patent Number: 5,321,037

[45] Date of Patent: Jun. 14, 1994

[54] ISOXAZOLE DERIVATIVES FOR USE AS CEREBRO-ACTIVE DRUGS AND CENTRAL MUSCLE RELAXANTS

[75] Inventors: Mitsuo Nagano; Junichi Sakai; Nobuyoshi Iwata; Kazuo Kobayashi; Masao Kozuka; Kenji Yoshimi; Katsunori Kato; Yoshiko Kubo; Toshiyuki Tonohiro; Takao Hara, all of Tokyo, Japan

[73] Assignee: Sankyo Company, Limited, Tokyo, Japan

[21] Appl. No.: 26,271

[22] Filed: Mar. 4, 1993

Related U.S. Application Data

[63] Continuation of Ser. No. 851,241, Mar. 13, 1992, abandoned, which is a continuation of Ser. No. 620,843, Nov. 30, 1990, abandoned, which is a continuation-in-part of Ser. No. 329,416, Mar. 27, 1989, abandoned, and Ser. No. 373,098, Jun. 28, 1989, abandoned, which is a continuation-in-part of Ser. No. 136,658, Dec. 22, 1987, abandoned, and Ser. No. 326,306, Mar. 21, 1989, abandoned.

[30] Foreign Application Priority Data

| Dec. 26, 1986 | [JP] | Japan | 61-312843 |
| Mar. 24, 1988 | [JP] | Japan | 63-70427 |
| Mar. 30, 1988 | [JP] | Japan | 63-77653 |
| Apr. 19, 1988 | [JP] | Japan | 63-94654 |
| May 24, 1988 | [JP] | Japan | 63-126761 |
| May 30, 1988 | [JP] | Japan | 63-132400 |
| May 31, 1988 | [JP] | Japan | 63-133433 |
| Jul. 26, 1988 | [JP] | Japan | 63-186131 |
| Nov. 14, 1988 | [JP] | Japan | 63-287314 |

[51] Int. Cl.$^5$ .......... C07D 261/20; C07D 261/12; A61K 31/42
[52] U.S. Cl. .......... 514/379; 514/233.8; 514/236.8; 514/380; 544/137; 544/367; 544/368; 548/241; 548/243; 546/198; 546/209; 546/270; 546/275
[58] Field of Search ........ 548/241, 243; 514/379, 514/380, 233.8, 236.8; 544/137, 367, 368; 546/198, 209, 270, 275

[56] References Cited

FOREIGN PATENT DOCUMENTS 273744 7/1988 European Pat. Off. .
52-31070 3/1977 Japan .
56-34674 4/1981 Japan .

OTHER PUBLICATIONS

Slawik, Acta Pol Pharm. 41 625 (1984).
Chemical Abstracts, vol. 104, No. 7, Feb. 17, 1986, p. 516, Abstract No. 50810 (published in USA).
Patent Abstracts of Japan, vol. 5, No. 89 (C-58), [761], Jun. 10, 1981 (published in Japan).
Chemical Abstracts, vol. 88, No. 9, Feb. 27, 1978, p. 388, Abstract No. 62379f (published in USA).
Chemical Abstracts, vol. 101, No. 1, Jul. 2, 1984, p. 605, Abstract No. 7077t (published USA).
Chem. Abstract, 95-97779H (1981) (published in USA).

Primary Examiner—Robert Gerstl
Attorney, Agent, or Firm—Frishauf, Holtz, Goodman & Woodward

[57] ABSTRACT

Compounds of formula (I):

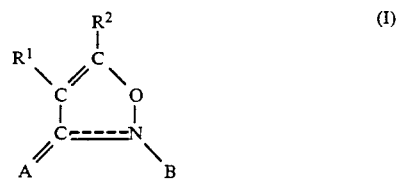

[in which: either (a) the dotted line ( ) is a single bond; A= is oxygen; and B is a group of formula (II):

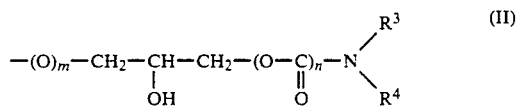

(in which m is 0 and n is 0 or 1) or (b) the dotted line (==) is a double bond; A= is said group of formula (II) in which m is 1 and n is 0 or 1; and B is absent; and R$^1$ is hydrogen, halogen, alkyl, alkenyl, alkynyl, optionally (Abstract continued on next page.)

ABSTRACT-continued substituted benzyl or optionally substituted phenyl; $R^2$ is hydrogen, halogen, alkyl, optionally substituted phenyl or heterocyclic; or $R^1$ and $R^2$, together with the carbon atoms to which they are attached, are a hydrocarbon ring fused to the isoxazole ring; $R^3$ and $R^4$ are each hydrogen, alkyl, optionally substituted benzyl or optionally substituted phenyl; or $R^3$, $R^4$ and the nitrogen atom to which they are attached together represent an alicyclic amino group]; and salts thereof may be used for the treatment of cerebral circulatory problems and for use as centrally acting muscle relaxants.

41 Claims, No Drawings

ISOXAZOLE DERIVATIVES FOR USE AS CEREBRO-ACTIVE DRUGS AND CENTRAL MUSCLE RELAXANTS

This application is a continuation of application Ser. No. 07/851,241, filed Mar. 13, 1992 (abandoned), which is a continuation of Ser. No. 07/620,843 filed on Nov. 30, 1990 (abandoned), which is a continuation-in-part of application Ser. No. 07/329,416 filed Mar. 27, 1989 (abandoned); and a continuation-in-part of application Ser. No. 07/373,098 filed Jun. 28, 1989 now abandoned, which is, in turn, a continuation-in-part of application Ser. No. 07/136,658 filed Dec. 22, 1987 (abandoned) and a continuation-in-part of application Ser. No. 07/326,306 filed Mar. 21, 1989 (abandoned).

BACKGROUND OF THE INVENTION

The present invention relates to a series of new isoxazole derivatives, which are regarded as derivatives of isoxazolones, and which may be used for the treatment of cerebral circulatory problems and for use as centrally acting muscle relaxants. The invention also provides methods of using these compounds and processes for preparing them.

Cerebrovascular disorders, including stroke infarction, are among the main causes of death in the world today. Moreover, although the patient may survive in such cases, cognition impairment, which may be one of the sequelae of the disease, is a substantial social problem at present. For this reason, the development of therapeutic agents for the treatment of such disorders (commonly referred to as "cerebro-active drugs") is required.

Moreover, rigidity and/or spasticity are often observed as the sequelae of cerebrovascular disorders, such as cerebral stroke infarction, or as cerebro-traumatic sequelae, and make rehabilitation difficult. Centrally-acting muscle relaxants are available which can relieve such spasrigido hemiplegia, and act on the central nervous system. Examples of existing centrally-acting muscle relaxants include eperisone hydrochloride and afloqualone.

An object of the present invention is to provide new compounds which can be used as cerebro-active drugs and as centrally-acting muscle relaxants. Such compounds are needed which can treat cerebral circulatory problems and alleviate myotony and spasrigido hemiplegia, preferably without giving rise to accompanying drowsiness.

It is also a related object to provide a method of treating cerebrovascular disorders by the administration to a mammal, which may be human, suffering from or prone to cerebrovascular disorders of at least one cerebro-active drug.

Certain isoxazolone derivatives within the scope of formula (I) of the present invention are known which have the required effect. For example, Japanese Patent Application Kokai (i.e. as laid open to public inspection) Sho. No. 56-34674, discloses such compounds having anti-inflammatory, analgesic and anti-pyretic activities.

Additionally, certain compounds closely related to those of the present invention are disclosed in Japanese Patent Application Kokai Sho. No. 52-31070 (published March 1977) as discussed in detail below.

BRIEF SUMMARY OF THE INVENTION

The present invention is directed to a series of isoxazole derivatives, which are capable of acting as cerebro-active drugs and as centrally acting muscle relaxants, their production, and their use.

The present invention accordingly provides compounds of formula (I);

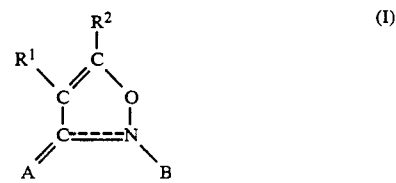

in which: either
(a) the dotted line (≏) represents a single bond;
A = represents a oxygen atom; and
B represents a group of formula (II):

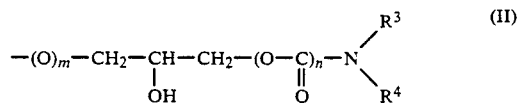

in which m is 0 and n is 0 or 1; or
(b) the dotted line (≏) represents a double bond;
A = represents said group of formula (II) in which m is 1 and n is 0 or 1; and
B is absent; and $R^1$ represents a hydrogen atom, a halogen atom, a a $C_1$-$C_4$ alkyl group, a $C_2$-$C_4$ alkenyl group, a $C_2$-$C_4$ alkynyl group, a benzyl group, a benzyl group having at least one substituent selected from the group consisting of substituents (a), defined below, a phenyl group or a phenyl group having at least one substituent selected from the group consisting of substituents (a), defined below;

$R^2$ represents a hydrogen atom, a halogen atom, a $C_1$-$C_4$ alkyl group, a phenyl group, a phenyl group having at least one substituent selected from the group consisting of substituents (a), defined below, or a heterocyclic group having 5 or 6 ring atoms, of which from 1 to 3 are hetero-atoms selected from the group consisting of nitrogen, oxygen and sulfur hetero-atoms, said heterocyclic group being unsubstituted or having at least one substituent selected from the group consisting of substituents (a), defined below; or $R^1$ and $R^2$, together with the carbon atoms to which they are attached, represent a hydrocarbon ring fused to the isoxazole ring and having, in total, from 5 to 7 ring carbon atoms, said hydrocarbon ring being unsubstituted or having at least one substituent selected from the group consisting of substituents (b), defined below;

$R^3$ and $R^4$ are independently selected from the group consisting of hydrogen atoms, $C_1$-$C_4$ alkyl groups, benzyl groups, benzyl groups having at least one substituent selected from the group consisting of substituents (a), defined below, phenyl groups and phenyl groups having at least one substituent selected from the group consisting of substituents (a), defined below; or $R^3$, $R^4$ and the nitrogen atom to which they are attached together represent an alicyclic amino group having a total of 5 or 6 ring atoms, of which one is said nitrogen atom and 0 or 1 is an additional hetero-atom selected from the group consisting of nitrogen, oxygen and sulfur hetero-atoms, said alicyclic amino group being unsubstituted or, where there is an additional nitrogen hetero-atom, having at least one substituent on that additional nitrogen hetero-atom selected from the group consisting of substituents (b), defined below;

substituents (a) can be:

$C_1$–$C_4$ alkyl groups, $C_1$–$C_4$ alkoxy groups, hydroxy groups, halogen atoms, nitro groups, amino groups, trifluoro amino and $C_2$–$C_4$ aliphatic carboxylic acylamino groups; or:

$C_1$–$C_3$ alkyl groups, $C_1$–$C_3$ alkoxy groups, hydroxy groups, halogen atoms, nitro groups, amino groups and $C_2$–$C_4$ aliphatic carboxylic acylamino groups; or: especially for compounds of the formula (I-a) wherein both m and n are 0:

$C_1$–$C_4$ alkyl groups, $C_1$–$C_4$ alkoxy groups, hydroxy groups, halogen atoms, nitro groups, and trifluoro amino groups;

substituents (b):

$C_1$–$C_3$ alkyl groups, $C_1$–$C_3$ alkoxy groups, hydroxy groups, halogen atoms, nitro groups, amino groups, $C_2$–$C_4$ aliphatic carboxylic acylamino groups, benzyl groups, benzyl groups having at least one substituent selected from the group consisting of substituents (a), defined above, phenyl groups and phenyl groups having at least one substituent selected from the group consisting of substituents (a), defined above;

provided that:

(i) where A represents said group of formula (II) and n is 0, $R_1$ and $R_2$ together represent a benzene ring fused to the isoxazole ring and $R_4$ represents an alkyl group, then $R_3$ does not represent a hydrogen atom; and pharmaceutically acceptable salts thereof.

The present invention also resides, in part, in the unexpected and unpredictable discovery of centrally-acting muscle relaxant activity in compounds of formula (I): There is no correlation between, on one hand, an activity as an anti-inflammatory, analgesic and antipyretic agent, and, on the other hand, and activity as a centrally-acting muscle relaxant agent.

The present invention also provides a method of treating cerebrovascular disorders by the administration to a mammal, which may be human, suffering from or prone to cerebrovascular disorders of at least one cerebro-active drug, wherein the cerebro-active drug is a compound of formula (I) (without the exclusionary proviso) or a pharmaceutically acceptable salt thereof.

The present invention also provides a method of effecting centrally-acting muscle relaxant activity, which comprises administering an active compound to a mammal, which may be human, wherein the active compound is a compound of formula (I) (without the exclusionary proviso) or a pharmaceutically acceptable salt thereof.

The invention also provides a pharmaceutical composition for the treatment of cerebrovascular disorders or as a centrally-acting muscle relaxant, which composition comprises an effective amount of an active compound, wherein the active compound is a compound of formula (I) (without the exclusionary proviso) or a pharmaceutically acceptable salt thereof.

The invention also provides processes for preparing the compounds of the present invention, which processes are described in more detail hereafter.

Compounds similar to those of formula (I), but in which B represents said group of formula (II) in which n is 0, and $R^1$ represents a hydrogen or halogen atom are disclosed in the aforementioned Japanese Patent Application Kokai Sho. No. 56-34674, although their cerebro-active and centrally-acting muscle relaxant properties are not disclosed therein. The present invention, therefore, also provides these compounds for use as cerebro-active drugs and centrally-acting muscle relaxants.

Compounds similar to those of formula (I), but in which A represents said group of formula (II) in which n is 0, $R^1$ and $R^2$ together represent a benzene ring fused to the isoxazole ring, $R^4$ represents an alkyl group and $R^3$ represents a hydrogen atom are disclosed in the aforementioned Japanese Patent Application Kokai Sho. No. 52-31070, although their cerebro-active and centrally-acting muscle relaxant properties are not disclosed therein. The present invention, therefore, also provides these compounds for use as cerebro-active drugs and centrally-acting muscle relaxants (although they are excluded from compound claims).

DETAILED DESCRIPTION OF THE INVENTION

In the compounds of the present invention, where $R^1$ represents $C_1$–$C_4$ alkyl group, this may be a straight or branched chain group and examples include the methyl, ethyl, propyl, isopropyl, butyl, isobutyl, sec-butyl and t-butyl groups, of which the methyl, ethyl, isopropyl and isobutyl groups are preferred.

Where $R^1$ represents a halogen atom, this may be a fluorine, chlorine, bromine or iodine atom, of which the fluorine, chlorine and bromine atoms are preferred, the chlorine atom being most preferred.

Where $R^1$ represents a $C_2$–$C_4$ alkenyl group, this may be a straight or branched chain group and examples include the vinyl, allyl, 1-propenyl, 1-butenyl, 2-butenyl, 3-butenyl, 3-methylallyl and 2-methylallyl groups, of which the vinyl, allyl, 2-butenyl, 3-methylallyl and 2-methylallyl groups are preferred.

Where $R^1$ represents a $C_2$–$C_4$ alkynyl group, this may be a straight or branched chain group and examples include the ethynyl, 1-propynyl, 2-propynyl, 1-butynyl, 2-butynyl and 3-butynyl groups, of which the ethynyl and 2-propynyl groups are most preferred.

Where $R^1$ represents a benzyl group, this may be unsubstituted or it may have one or more substituents. If it is substituted, it may have from 1 to 5 substituents, more preferably from 1 to 3 substituents, and most preferably 1 or 2 substituents, which may be selected from the group consisting of substituents (a), defined above and exemplified below. Examples of such optionally substituted benzyl groups include the benzyl group itself, and the 2-chlorobenzyl, 3-chlorobenzyl, 4-chlorobenzyl, 2-fluorobenzyl, 3-fluorobenzyl, 4-fluorobenzyl, 2-bromobenzyl, 3-bromobenzyl, 4-bromobenzyl, 2-nitrobenzyl, 3-nitrobenzyl, 4-nitrobenzyl, 2-methoxybenzyl, 3-methoxybenzyl, 4-methoxybenzyl, 2-propoxybenzyl, 3-Propoxybenzyl, 4-Propoxybenzyl, 2-hydroxybenzyl, 3-hydroxybenzyl, 4-hydroxybenzyl, 2-aminobenzyl, 3-aminobenzyl, 4-aminobenzyl, 2-propylbenzyl, 3-propylbenzyl, 4-Propylbenzyl, 2-methylbenzyl, 3-methylbenzyl, 4-methylbenzyl, 2-acetylbenzyl, 3-acetylbenzyl, 4-acetylbenzyl, 2-butyrylbenzyl, 3-butyrylbenzyl, 4-butyrylbenzyl, 2,4-dichlorobenzyl, 2,4-difluorobenzyl, 2-chloro-4-fluorobenzyl, 2-chloro-4-butylbenzyl, 3,5-dichlorobenzyl, 3,5-difluorobenzyl, 3-chloro-5-fluorobenzyl and 3-chloro-5-butylbenzyl groups, but the benzyl group itself is preferred.

Where $R_1$ is a phenyl group, this may be unsubstituted or it may have one or more substituents. If it is substituted, it may have from 1 to 5 substituents, more preferably from 1 to 3 substituents, and most preferably 1 or 2 substituents, which may be selected from the group consisting of substituents (a), defined above and exemplified below. Examples of such optionally substituted phenyl groups include the phenyl group itself, and the 2-chlorophenyl, 3-chlorophenyl, 4-chlorophenyl, 2-fluorophenyl, 3-fluorophenyl, 4-fluorophenyl, 2-bromophenyl, 3-bromophenyl, 4-bromophenyl, 2-nitrophenyl, 3-nitrophenyl, 4-nitrophenyl, 2-methoxyphenyl, 3-methoxyphenyl, 4-methoxyphenyl, 2-propoxyphenyl, 3-propoxyphenyl, 4-propoxyphenyl, 2-hydroxyphenyl, 3-hydroxyphenyl, 4-hydroxyphenyl, 2-aminophenyl, 3-aminophenyl, 4-aminophenyl, 2-propylphenyl, 3-propylphenyl, 4-propylphenyl, 2-methylphenyl, 3-methylphenyl, 4-methylphenyl, 2-acetylphenyl, 3-acetylphenyl, 4-acetylphenyl, 2-butyrylphenyl, 3-butyrylphenyl, 4-butyrylphenyl, 2,4-dichlorophenyl, 2,4-difluorophenyl, 2-chloro-4-fluorophenyl, 2-chloro-4-butylphenyl, 3,5-dichlorophenyl, 3,5-difluorophenyl, 3-chloro-5-fluorophenyl and 3-chloro-5-butylphenyl groups, but the phenyl group itself is preferred.

In general, preferred groups and atoms which may be represented by $R^1$ include the hydrogen and chlorine atoms, and the methyl, ethyl, isopropyl, isobutyl, allyl, 3-methylallyl, 2-propynyl, phenyl and benzyl groups.

Where $R^2$ represents a halogen atom, this may be as exemplified above in relation to the halogen atoms which may be represented by $R^1$, and preferred halogen atoms are also as exemplified in relation to $R^1$.

Where $R^2$ represents an alkyl group, this may be as exemplified above in relation to the alkyl groups which may be represented by $R^1$. Preferred alkyl groups are the methyl, ethyl, propyl, isopropyl, butyl, isobutyl, sec-butyl and t-butyl groups, of which the methyl group is most preferred.

Where $R^2$ represents a phenyl group, this may be as exemplified above in relation to the optionally substituted phenyl groups which may be represented by $R^1$. Preferred optionally substituted phenyl groups for $R^2$ are the phenyl group itself, and the 4-chlorophenyl, 3-chlorophenyl, 4-nitrophenyl, 4-methoxyphenyl, 3-methoxyphenyl, 2-methoxyphenyl, 4-hydroxyphenyl, 4-fluorophenyl and 2,4-dichlorophenyl groups.

Where $R^2$ represents a heterocyclic group having 5 or 6 ring atoms, from 1 to 3 of these are hetero-atoms selected from the group consisting of nitrogen, oxygen and sulfur hetero-atoms, and said heterocyclic group is unsubstituted or has at least one substituent selected from the group consisting of substituents (a), defined above and exemplified below. In general, the number of such substituents may be from 1 to 5, although the preferred number is from 1 to 3, more preferably 1 or 2. The heterocyclic group may be aromatic or non-aromatic in character, although it is preferably aromatic. Examples of such heterocyclic groups include the thienyl, furyl, pyranyl, pyrrolyl, imidazolyl, pyrazolyl, thiazolyl, isothiazolyl, oxazolyl, isoxazolyl, pyridyl, pyrazinyl, pyrimidinyl, pyridazinyl, furazanyl, pyrrolidinyl, pyrrolinyl, imidazolidinyl, imidazolinyl, pyrazolidinyl, pyrazolinyl, piperidyl, piperazinyl, morpholinyl and thiomorpholinyl groups. Examples of such substituted heterocyclic groups include the 6-chloro-3-pyridyl, 6-(trifluoromethyl)-3-pyridyl, 5-chloro-2-pyridyl, 5-(trifluoromethyl)-2-furyl and 5-(trifluoromethyl)-2-thienyl and 5-chloro-2-thienyl groups. The preferred groups are the thiazolyl, furyl, thienyl and pyridyl groups, of which the thienyl and pyridyl groups, still more preferably the 2-thienyl and 3-pyridyl groups, are most preferred, and these may be unsubstituted or substituted as defined above.

Where $R^1$ and $R^2$, together with the carbon atoms to which they are attached, represent a hydrocarbon ring fused to the isoxazole ring and having, in total, from 5 to 7 ring carbon atoms, the hydrocarbon ring may be unsubstituted or may have at least one substituent selected from the group consisting of substituents (b), defined above and exemplifed below. Such a hydrocarbon group may be wholly (i.e. aromatically) or partially unsaturated, but is preferably aromatic in character. Examples of 5 to 7 membered ring systems that may be formed by $R^1$ and $R^2$, together with the carbon atoms to which they are attached, include the benzene, cyclohexene, cyclohexadiene, cyclopentene, cyclopentadiene, cycloheptene, cycloheptadiene and cycloheptatriene ring systems, of which the multiply unsaturated groups are preferred, the benzene ring being most preferred. Such ring systems may be unsubstituted or may have at least one substituent selected from the group consisting of substituents (a), defined above and exemplified below. The maximum number of substituents is limited only by the number of substitutable positions on the hydrocarbon ring, although, in the case of "bulky" substituents, steric constraints may also apply. Preferred substituted and unsubstituted ring systems are (including the isoxazole ring to which they are attached): the 1,2-benzisoxazole, 5-chloro-1,2-benzisoxazole, 5-amino-1,2-benzisoxazole, 5-acetamido-1,2-benzisoxazole, 5-methoxy-1,2-benzisoxazole, 6-chloro-1,2-benzisoxazole, 4-chloro-1,2-benzisoxazole, 7-chloro-1,2-benzisoxazole, 5-methyl-1,2-benzisoxazole, 5,6-dichloro-1,2-benzisoxazole, 4,5,6,7-tetrachloro-1,2-benzisoxazole, 5-propyl-1,2-benzisoxazole, 5-ethoxy-1,2-benzisoxazole, 5-phenyl-1,2-benzisoxazole, 5-benzyl-1,2-benzisoxazole, 5-(4-chlorophenyl)-1,2-benzisoxazole and 5-(4-chlorobenzyl)-1,2-benzisoxazole groups. Of these, we prefer the 1,2-benzisoxazole, 5-chloro-1,2-benzisoxazole, 5-amino-1,2-benzisoxazole, 5-acetamido-1,2-benzisoxazole, 5-methoxy-1,2-benzisoxazole and 6-chloro-1,2-benzisoxazole groups.

Where $R^3$ and/or $R^4$ represents a $C_1$–$C_4$ alkyl group, a benzyl group, a benzyl group having at least one substituent selected from the group consisting of substituents (a), defined above and exemplified below, a phenyl group or a phenyl group having at least one substituent selected from the group consisting of substituents (a), defined above and exemplified below, then examples of such groups are as exemplified above in relation to the same groups which may be represented by $R^1$. Preferred groups and atoms which may be represented by $R^3$ and/or $R^4$ include the hydrogen atom, and the methyl, ethyl, propyl, isopropyl, butyl, isobutyl, sec-butyl, t-butyl, phenyl and benzyl groups, the hydrogen atom being most preferred. The two groups $R^3$ and $R^4$ may be the same or different; where they are different, the most preferred groups are those in which one of $R^3$ and $R^4$ represents a hydrogen atom and the other represents one of the other groups defined above, more preferably an alkyl group.

Hence, preferred groups represented by $—NH^3R^4$ include the amino, methylamino, ethylamino, propylamino, isopropylamino, butylamino, isobutylamino, sec-butylamino, t-butylamino, dimethylamino, diethylamino, phenylamino and benzylamino groups.

Alternatively, $R^3$, $R^4$ and the nitrogen atom to which they are attached may together represent an alicyclic amino group having a total of 5 or 6 ring atoms, of which one is said nitrogen atom and 0 or 1 is an additional hetero-atom selected from the group consisting of nitrogen, oxygen and sulfur hetero-atoms, said alicyclic amino group being unsubstituted or, where there is an additional nitrogen hetero-atom, having at least one substituent on that additional nitrogen hetero-atom selected from the group consisting of substituents (b), defined above and exemplified below. Examples of such groups include the 1-pyrrolyl, 1-imidazolyl, 1-pyrazolyl, 3-thiazolyl, 2-isothiazolyl, 3-oxazolyl, 2-isoxazolyl, 1-pyridyl, 1-pyrazinyl, 1-pyrimidinyl, 1-pyridazinyl, 2-furazanyl, 1-pyrrolidinyl, 1-pyrrolinyl, 1-imidazolidinyl, 1-imidazolinyl, 1-pyrazolidinyl, 1-pyrazolinyl, piperidino, 1-piperazinyl, morpholino and thiomorpholino groups, which may be substituted or unsubstituted, and, if substituted, the substituents are selected from the group consisting of substituents (b), defined above and exemplified below. Of these, the morpholino, 1-piperazinyl, 4-methyl-1-piperazinyl, 1-pyrrolidinyl and piperidino groups are most preferred.

Examples of groups and atoms included in substituents (a) include:

$C_1$–$C_3$ alkyl groups, such as the methyl, ethyl, propyl and isopropyl groups;

$C_1$–$C_3$ alkoxy groups, such as the methoxy, ethoxy, propoxy and isopropoxy groups;

the hydroxy, nitro and amino groups;

halogen atoms, such as the fluorine, chlorine, bromine and iodine atoms; and $C_2$–$C_4$ aliphatic carboxylic acylamino groups, especially the $C_2$–$C_4$ alkanoylamino groups, such as the acetamido, propionamido, butyramido, isobutyramido, acryloylamino, propioloylamino, methacryloylamino, crotonoylamino and isocrotonoylamino groups.

Examples of groups and atoms incouded in substituents (b) include those exemplified above in relation to substituents (a) and optionally substituted phenyl and benzyl groups, such as those exemplified above in relation to the same groups which may be represented by $R^1$.

Preferred classes of compounds of the present invention are the following compounds:

(a) compounds of formula (Ia):

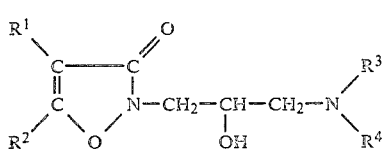

in which:

$R^1$ represents a $C_1$–$C_4$ alkyl group, a $C_2$–$C_4$ alkenyl group, a $C_2$–$C_4$ alkynyl group, a benzyl group, a substituted benzyl group, a phenyl group or a substituted phenyl group, the substituents being selected from the group consisting of substituents (a), defined above;

$R^2$ represents hydrogen atom, a $C_1$–$C_4$ alkyl group, a phenyl group, a substituted phenyl group, or a heterocyclic group as defined above;

$R^3$ and $R^4$ are independently selected from the group consisting of hydrogen atoms, $C_1$–$C_4$ alkyl groups, benzyl groups, substituted benzyl groups, phenyl groups and substituted phenyl groups, or $R^3$ and $R^4$ may be taken together with the nitrogen atom to which they are attached to form an alicyclic amino group, as defined above;

(b) compounds of formula (Ib):

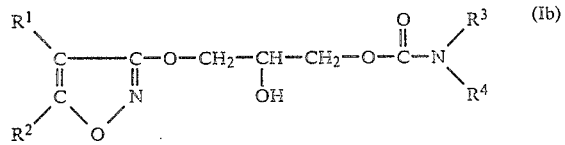

in which:

$R^1$ represents a hydrogen atom, a halogen atom, a $C_1$–$C_4$ alkyl group, a $C_2$–$C_4$ alkenyl group, a $C_2$–$C_4$ alkynyl group, a benzyl group, a benzyl group having at least one substituent selected from the group consisting of substituents (a), defined above, a phenyl group or a phenyl group having at least one substituent selected from the group consisting of substituents (a), defined above;

$R^2$ represents a hydrogen atom, a $C_1$–$C_4$ alkyl group, phenyl group, a phenyl group having at least one substituent selected from the group consisting of substituents (a), defined above, or a heterocyclic group as defined above; or $R^1$ and $R^2$, together with the carbon atoms to which they are attached, represent a hydrocarbon ring fused to the isoxazole ring and as defined above;

$R^3$ and $R^4$ are independently selected from the group consisting of hydrogen atoms, $C_1$–$C_4$ alkyl groups, benzyl groups, benzyl groups having at least one substituent selected from the group consisting of substituents (a), defined above, phenyl groups and phenyl groups having at least one substituent selected from the group consisting of substituents (a), defined above; or $R^3$, $R^4$ and the nitrogen atom to which they are attached together represent an alicyclic amino group as defined above;

(c) compounds of formula (Ic):

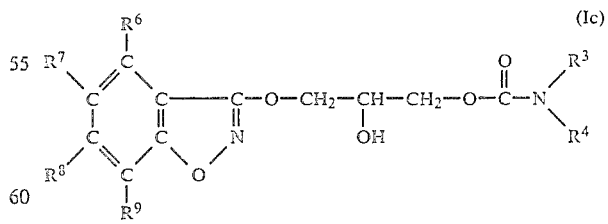

in which:

$R^3$ and $R^4$ are as defined above in class (b); and one of $R^6$, $R^7$, $R^8$ and $R^9$ represents a hydrogen atom, a halogen atom, a $C_1$–$C_4$ alkyl group or a $C_1$–$C_4$ alkoxy group, and the others all represent hydrogen atoms;

(d) compounds of formula (Id):

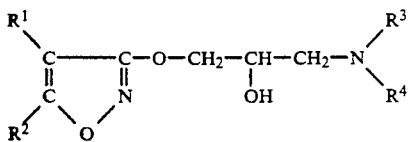

in which:

$R^1$, $R^2$, $R^3$ and $R^4$ are as defined above in class (b), provided that, where $R^1$ and $R^2$ together represent a benzene ring fused to the isoxazole ring and $R^4$ represents an alkyl group, then $R^3$ does not represent a hydrogen atom;

(e) compounds of formula (Ie):

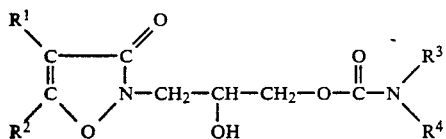

in which:

$R^1$, $R^2$, $R^3$ and $R^4$ are as defined above in class (b);

(f) compounds of formula (If):

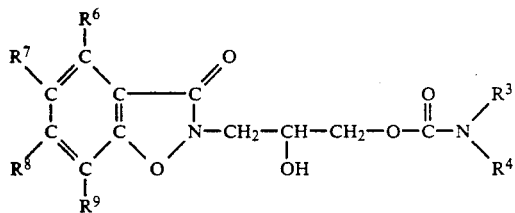

in which:

$R^3$ and $R^4$ are as defined above in class (b); and
$R^6$, $R^7$, $R^8$ and $R^9$ are as defined above in class (c);
and pharmaceutically acceptable salts thereof.

Especially preferred classes of compounds of the present invention are those compounds of formulae (I), (Ia), (Ib), (Ic), (Id), (Ie) and (If), shown above, in which:

(A) $R^1$ represents a hydrogen atom, a halogen atom or a $C_1$-$C_4$ alkyl group;

(B) $R^2$ represents a phenyl group or a phenyl group having at least one substituent selected from the group consisting of substituents (c), defined below;

substituents (c):

$C_1$-$C_3$ alkoxy groups, hydroxy groups and halogen atoms;

(C) $R^1$ and $R^2$, together with the carbon atoms to which they are attached, represent a 6-membered hydrocarbon ring fused to the isoxazole ring and being unsubstituted or having at least one substituent selected from the group consisting of halogen atoms;

(D) $R^3$ and $R^4$ are independently selected from the group consisting of hydrogen atoms, $C_1$-$C_4$ alkyl groups, benzyl groups and phenyl groups;

(E) $R^3$, $R^4$ and the nitrogen atom to which they are attached together represent an alicyclic amino group having a total of 5 or 6 ring atoms, of which one is said nitrogen atom and 0 or 1 is an additional nitrogen hetero-atom, said alicyclic amino group being unsubstituted or, where there is an additional nitrogen hetero-atom, having at least one substituent on that additional nitrogen hetero-atom selected from the group consisting of substituents (d), defined below;

substituents (d):

$C_1$-$C_3$ alkyl groups, benzyl groups and phenyl groups;

and the most preferred compounds of the present invention are those compounds of formulae (I), (Ia), (Ib), (Ic), (Id) and (Ie), shown above, in which:

(F) $R^1$ represents a hydrogen atom, a chlorine atom or a $C_1$ or $C_2$ alkyl group;

(G) $R^2$ represents a phenyl group or a phenyl group having at least one substituent selected from the group consisting of substituents (c'), defined below;

substituents (c'):

methoxy groups and halogen atoms;

(H) $R^1$ and $R^2$, together with the carbon atoms to which they are attached, represent a benzene ring fused to the isoxazole ring and being unsubstituted or having one substituent selected from the group consisting of halogen atoms;

(I) $R^3$ and $R^4$ are independently selected from the group consisting of hydrogen atoms, methyl groups and ethyl groups;

(J) $R^3$, $R^4$ and the nitrogen atom to which they are attached together represent a morpholino group, a 1-piperazinyl group, a 4-methyl-1-piperazinyl group, a 1-pyrrolidinyl group or a piperidino group;

and pharmaceutically acceptable salts thereof.

The compounds of the present invention necessarily contain several basic nitrogen atoms and can, therefore, form acid addition salts and such salts also form part of the present invention. There is no limitation upon the nature of such salts, provided that, where they are to be used for therapeutic purposes, they are pharmaceutically acceptable, which, as is well-known in the art, means that they do not have reduced activity (or unacceptably reduced activity) or increased toxicity (or unacceptably increased toxicity) compared with the free compound of formula (I). Where, however, they are to be used for non-therapeutic purposes, e.g. as intermediates in the preparation of other compounds, even this limitation does not apply. Examples of suitable salts include: salts with an inorganic acid, such as a hydrogen halide (e.g. hydrofluoric acid, hydrochloric acid, hydrobromic acid or hydroiodic acid), or nitric acid, perchloric acid, sulfuric acid or phosphoric acid; and salts with an organic acid, such as a lower alkylsulfonic acid (e.g. methanesulfonic acid, trifluoromethanesulfonic acid or ethanesulfonic acid), an arylsulfonic acid (e.g. benzenesulfonic acid or p-toluenesulfonic acid), or a carboxylic acid (e.g. fumaric acid, lactic acid, citric acid, tartaric acid, succinic acid, oxalic acid or maleic acid).

The compounds of the present invention can exist in the form of various optical isomers and diastereomers because of the existence of asymmetric carbon atoms in the molecule. The optical isomers can be resolved using conventional techniques of optical resolution to give optically active compounds. The present invention covers both the individual isomers and mixtures (e.g. racemic mixtures) thereof, whether as obtained by their synthesis reaction or by mixing. If individual isomers are required, these may be prepared from mixtures, by conventional means, or they may be prepared by stereospecific synthesis techniques, as are well known in the art.

Examples of specific compounds of the invention are given in the following formulae (I-1) to (I-4), in which the substituents are as defined in the corresponding one of Tables 1 to 4, respectively [i.e. Table 1 relates to formula (I-1), Table 2 relates to formula (I-2) and so on]. In the Tables, the following abbreviations are used:

| | |
|---|---|
| Ac | acetyl |
| All | allyl |
| Bu | butyl |
| iBu | isobutyl |
| sBu | sec-butyl |
| tBu | t-butyl |
| Bz | benzyl |
| Et | ethyl |
| Me | methyl |
| Mor | morpholino |
| Ph | phenyl |
| Pip | piperidyl |
| Piz | piperazinyl |
| Pr | propyl |
| iPr | isopropyl |
| Pyr | pyridyl |
| Pyrd | pyrrolidinyl |
| Thi | thienyl |

$$\text{(I-1)} \quad \underset{R^2}{\overset{R^1}{\underset{|}{C}}} \underset{O}{\overset{\parallel}{C}} \underset{\parallel}{\overset{O}{C}} N-CH_2-\underset{OH}{\overset{|}{C}H}-CH_2-(O-\overset{\parallel}{C})_n-R^5$$

$$\text{(I-2)} \quad \text{benzisoxazolone with } R^6, R^7, R^8, R^9, R^2 \text{ substituents}, \; N-CH_2-\underset{OH}{\overset{|}{C}H}-CH_2-O-\overset{\overset{O}{\parallel}}{C}-R^5$$

$$\text{(I-3)} \quad \underset{R^2}{\overset{R^1}{\underset{|}{C}}} \text{ isoxazole } -C-O-CH_2-\underset{OH}{\overset{|}{C}H}-CH_2-(O-\overset{\overset{O}{\parallel}}{C})_n-R^5$$

$$\text{(I-4)} \quad \text{benzisoxazole with } R^6, R^7, R^8, R^9\text{-substituents } -C-O-CH_2-\underset{OH}{\overset{|}{C}H}-CH_2-(O-\overset{\overset{O}{\parallel}}{C})_n-R^5$$

TABLE 1

| CPd No. | $R^1$ | $R^2$ | $R^5$ | n |
|---|---|---|---|---|
| 1-1 | Me | Ph | —NH$_2$ | 0 |
| 1-2 | Me | Ph | —NHMe | 0 |
| 1-3 | Me | Ph | —NHEt | 0 |
| 1-4 | Me | Ph | —NHPr | 0 |
| 1-5 | Me | Ph | —NHiPr | 0 |
| 1-6 | Me | Ph | —NHBu | 0 |
| 1-7 | Me | Ph | —NHiBu | 0 |
| 1-8 | Me | Ph | —NHsBu | 0 |
| 1-9 | Me | Ph | —NHtBu | 0 |
| 1-10 | Me | Ph | —NHPh | 0 |
| 1-11 | Me | Ph | —NHBz | 0 |
| 1-12 | Me | Ph | 1-Pyrd | 0 |
| 1-13 | Me | Ph | Mor | 0 |
| 1-14 | Me | Ph | 1-Piz | 0 |
| 1-15 | Me | Ph | 4-Me-1-Piz | 0 |
| 1-16 | Et | Ph | Mor | 0 |

TABLE 1-continued

| CPd No. | $R^1$ | $R^2$ | $R^5$ | n |
|---|---|---|---|---|
| 1-17 | iPr | Ph | Mor | 0 |
| 1-18 | iBu | Ph | Mor | 0 |
| 1-19 | All | Ph | Mor | 0 |
| 1-20 | MeCH=CHCH$_2$— | Ph | Mor | 0 |
| 1-21 | HC≡C—CH$_2$— | Ph | Mor | 0 |
| 1-22 | Ph | Ph | Mor | 0 |
| 1-23 | Bz | Ph | Mor | 0 |
| 1-24 | Me | Me | Mor | 0 |
| 1-25 | Me | Et | Mor | 0 |
| 1-26 | Me | Pr | Mor | 0 |
| 1-27 | Me | iPr | Mor | 0 |
| 1-28 | Me | Bu | Mor | 0 |
| 1-29 | Me | iBu | Mor | 0 |
| 1-30 | Me | sBu | Mor | 0 |
| 1-31 | Me | tBu | Mor | 0 |
| 1-32 | Me | H | Mor | 0 |
| 1-33 | Me | 4-ClPh | Mor | 0 |
| 1-34 | Me | 3-ClPh | Mor | 0 |
| 1-35 | Me | 2-ClPh | Mor | 0 |
| 1-36 | Me | 4-NO$_2$Ph | Mor | 0 |
| 1-37 | Me | 4-MeOPh | Mor | 0 |
| 1-38 | Me | 3-MeOPh | Mor | 0 |
| 1-39 | Me | 2-MeOPh | Mor | 0 |
| 1-40 | Me | 2-HOPh | Mor | 0 |
| 1-41 | Me | 2,4-diClPh | Mor | 0 |
| 1-42 | Me | 4-FPh | Mor | 0 |
| 1-43 | Me | 2-Thi | Mor | 0 |
| 1-44 | Me | 3-Pyr | Mor | 0 |
| 1-45 | H | Ph | —NH$_2$ | 1 |
| 1-46 | H | Ph | —NHMe | 1 |
| 1-47 | H | Ph | —NHEt | 1 |
| 1-48 | H | Ph | —NHPr | 1 |
| 1-49 | H | Ph | —NHiPr | 1 |
| 1-50 | H | Ph | —NHBu | 1 |
| 1-51 | H | Ph | —NHiBu | 1 |
| 1-52 | H | Ph | —NHsBu | 1 |
| 1-53 | H | Ph | —NHtBu | 1 |
| 1-54 | H | Ph | —NHPh | 1 |
| 1-55 | H | Ph | —NHBz | 1 |
| 1-56 | H | Ph | —NMe$_2$ | 1 |
| 1-57 | H | Ph | 1-Pyrd | 1 |
| 1-58 | H | Ph | Mor | 1 |
| 1-59 | H | Ph | 1-Piz | 1 |
| 1-60 | H | Ph | 4-Me-1-Piz | 1 |
| 1-61 | H | Ph | 1-Pip | 1 |
| 1-62 | Cl | Ph | —NH$_2$ | 1 |
| 1-63 | Cl | Ph | —NHMe | 1 |
| 1-64 | Cl | Ph | —NHEt | 1 |
| 1-65 | Cl | Ph | —NHPr | 1 |
| 1-66 | Cl | Ph | —NHiPr | 1 |
| 1-67 | Cl | Ph | —NHBu | 1 |
| 1-68 | Cl | Ph | —NHiBu | 1 |
| 1-69 | Cl | Ph | —NHsBu | 1 |
| 1-70 | Cl | Ph | —NHtBu | 1 |
| 1-71 | Cl | Ph | —NHPh | 1 |
| 1-72 | Cl | Ph | —NHBz | 1 |
| 1-73 | Cl | Ph | —NMe$_2$ | 1 |
| 1-74 | Cl | Ph | 1-Pyrd | 1 |
| 1-75 | Cl | Ph | Mor | 1 |
| 1-76 | Cl | Ph | 1-Piz | 1 |
| 1-77 | Cl | Ph | 4-Me-1-Piz | 1 |
| 1-78 | Cl | Ph | 1-Pip | 1 |
| 1-79 | Me | Ph | —NH$_2$ | 1 |
| 1-80 | Et | Ph | —NH$_2$ | 1 |
| 1-81 | iPr | Ph | —NH$_2$ | 1 |
| 1-82 | iBu | Ph | —NH$_2$ | 1 |
| 1-83 | All | Ph | —NH$_2$ | 1 |
| 1-84 | MeCH=CHCH$_2$— | Ph | —NH$_2$ | 1 |
| 1-85 | HC≡C—CH$_2$— | Ph | —NH$_2$ | 1 |
| 1-86 | Ph | Ph | —NH$_2$ | 1 |
| 1-87 | Bz | Ph | —NH$_2$ | 1 |
| 1-88 | H | H | —NH$_2$ | 1 |
| 1-89 | H | Me | —NH$_2$ | 1 |
| 1-90 | H | Et | —NH$_2$ | 1 |
| 1-91 | H | Pr | —NH$_2$ | 1 |
| 1-92 | H | iPr | —NH$_2$ | 1 |
| 1-93 | H | Bu | —NH$_2$ | 1 |
| 1-94 | H | iBu | —NH$_2$ | 1 |
| 1-95 | H | sBu | —NH$_2$ | 1 |
| 1-96 | H | tBu | —NH$_2$ | 1 |

TABLE 1-continued

| Cpd No. | R¹ | R² | R⁵ | n |
|---|---|---|---|---|
| 1-97 | Cl | Me | —NH$_2$ | 1 |
| 1-98 | H | 4-ClPh | —NH$_2$ | 1 |
| 1-99 | H | 2-ClPh | —NH$_2$ | 1 |
| 1-100 | H | 3-ClPh | —NH$_2$ | 1 |
| 1-101 | H | 4-NO$_2$Ph | —NH$_2$ | 1 |
| 1-102 | H | 4-MeOPh | —NH$_2$ | 1 |
| 1-103 | H | 3-MeOPh | —NH$_2$ | 1 |
| 1-104 | H | 2-MeOPh | —NH$_2$ | 1 |
| 1-105 | H | 4-HOPh | —NH$_2$ | 1 |
| 1-106 | H | 4-FPh | —NH$_2$ | 1 |
| 1-107 | H | 2,4-diClPh | —NH$_2$ | 1 |
| 1-108 | H | 2-Thi | —NH$_2$ | 1 |
| 1-109 | H | 3-Pyr | —NH$_2$ | 1 |

TABLE 2

| Cpd. No. | R⁶ | R⁷ | R⁸ | R⁹ | R⁵ |
|---|---|---|---|---|---|
| 2-1 | H | H | H | H | —NH$_2$ |
| 2-2 | H | H | H | H | —NHMe |
| 2-3 | H | H | H | H | —NHEt |
| 2-4 | H | H | H | H | —NHPr |
| 2-5 | H | H | H | H | —NHiPr |
| 2-6 | H | H | H | H | —NHBu |
| 2-7 | H | H | H | H | —NHiBu |
| 2-8 | H | H | H | H | —NHsBu |
| 2-9 | H | H | H | H | —NHtBu |
| 2-10 | H | H | H | H | —NHPh |
| 2-11 | H | H | H | H | —NHBz |
| 2-12 | H | H | H | H | —NMe$_2$ |
| 2-13 | H | H | H | H | 1-Pyrd |
| 2-14 | H | H | H | H | Mor |
| 2-15 | H | H | H | H | 1-Piz |
| 2-16 | H | H | H | H | 4-Me-1-Piz |
| 2-17 | H | H | H | H | 1-Pip |
| 2-18 | H | Cl | H | H | —NHMe |
| 2-19 | H | Cl | H | H | —NHEt |
| 2-20 | H | Cl | H | H | —NHPr |
| 2-21 | H | Cl | H | H | —NHiPr |
| 2-22 | H | Cl | H | H | —NHBu |
| 2-23 | H | Cl | H | H | —NHiBu |
| 2-24 | H | Cl | H | H | —NHsBu |
| 2-25 | H | Cl | H | H | —NHtBu |
| 2-26 | H | Cl | H | H | —NHPh |
| 2-27 | H | Cl | H | H | —NHBz |
| 2-28 | H | Cl | H | H | —NMe$_2$ |
| 2-29 | H | Cl | H | H | 1-Pyrd |
| 2-30 | H | Cl | H | H | Mor |
| 2-31 | H | Cl | H | H | 1-Piz |
| 2-32 | H | Cl | H | H | 4-Me-1-Piz |
| 2-33 | H | Cl | H | H | 1-Pip |
| 2-34 | H | Cl | H | H | —NH$_2$ |
| 2-35 | H | H | H | Me | —NH$_2$ |
| 2-36 | H | —NH$_2$ | H | H | —NH$_2$ |
| 2-37 | H | —NHAc | H | H | —NH$_2$ |
| 2-38 | H | —OMe | H | H | —NH$_2$ |

TABLE 3

| Cpd No. | R¹ | R² | R⁵ | n |
|---|---|---|---|---|
| 3-1 | H | Ph | —NH$_2$ | 1 |
| 3-2 | H | Ph | —NHMe | 1 |
| 3-3 | H | Ph | —NHEt | 1 |
| 3-4 | H | Ph | —NHPr | 1 |
| 3-5 | H | Ph | —NHiPr | 1 |
| 3-6 | H | Ph | —NHBu | 1 |
| 3-7 | H | Ph | —NHiBu | 1 |
| 3-8 | H | Ph | —NHsBu | 1 |
| 3-9 | H | ph | —NHtBu | 1 |
| 3-10 | H | Ph | —NHPh | 1 |
| 3-11 | H | Ph | —NHBz | 1 |
| 3-12 | H | Ph | —NMe$_2$ | 1 |
| 3-13 | H | Ph | 1-Pyrd | 1 |
| 3-14 | H | Ph | Mor | 1 |
| 3-15 | H | Ph | 1-Piz | 1 |
| 3-16 | H | Ph | 4-Me-1-Piz | 1 |
| 3-17 | H | Ph | 1-Pip | 1 |
| 3-18 | Cl | Ph | —NH$_2$ | 1 |
| 3-19 | Cl | Ph | —NHMe | 1 |
| 3-20 | Cl | Ph | —NHEt | 1 |
| 3-21 | Cl | Ph | —NHPr | 1 |
| 3-22 | Cl | Ph | —NHiPr | 1 |
| 3-23 | Cl | Ph | —NHBu | 1 |
| 3-24 | Cl | Ph | —NHiBu | 1 |
| 3-25 | Cl | Ph | —NHsBu | 1 |
| 3-26 | Cl | Ph | —NHtBu | 1 |
| 3-27 | Cl | Ph | —NHPh | 1 |
| 3-28 | Cl | Ph | —NHBz | 1 |
| 3-29 | Cl | Ph | —NMe$_2$ | 1 |
| 3-30 | Cl | Ph | 1-Pyrd | 1 |
| 3-31 | Cl | Ph | Mor | 1 |
| 3-32 | Cl | Ph | 1-Piz | 1 |
| 3-33 | Cl | Ph | 4-Me-1-Piz | 1 |
| 3-34 | Cl | Ph | 1-Pip | 1 |
| 3-35 | Me | Ph | —NH$_2$ | 1 |
| 3-36 | Et | Ph | —NH$_2$ | 1 |
| 3-37 | iPr | Ph | —NH$_2$ | 1 |
| 3-38 | iBu | Ph | —NH$_2$ | 1 |
| 3-39 | All | Ph | —NH$_2$ | 1 |
| 3-40 | MeCH=CHCH$_2$— | Ph | —NH$_2$ | 1 |
| 3-41 | HC≡C—CH$_2$— | Ph | —NH$_2$ | 1 |
| 3-42 | Ph | Ph | —NH$_2$ | 1 |
| 3-43 | Bz | Ph | —NH$_2$ | 1 |
| 3-44 | H | H | —NH$_2$ | 1 |
| 3-45 | H | Me | —NH$_2$ | 1 |
| 3-46 | H | Et | —NH$_2$ | 1 |
| 3-47 | H | Pr | —NH$_2$ | 1 |
| 3-48 | H | iPr | —NH$_2$ | 1 |
| 3-49 | H | Bu | —NH$_2$ | 1 |
| 3-50 | H | iBu | —NH$_2$ | 1 |
| 3-51 | H | sBu | —NH$_2$ | 1 |
| 3-52 | H | tBu | —NH$_2$ | 1 |
| 3-53 | Cl | Me | —NH$_2$ | 1 |
| 3-54 | H | 4-ClPh | —NH$_2$ | 1 |
| 3-55 | H | 3-ClPh | —NH$_2$ | 1 |
| 3-56 | H | 4-NO$_2$Ph | —NH$_2$ | 1 |
| 3-57 | H | 4-MeOPh | —NH$_2$ | 1 |
| 3-58 | H | 3-MeOPh | —NH$_2$ | 1 |
| 3-59 | H | 2-MeOPh | —NH$_2$ | 1 |
| 3-60 | H | 4-HOPh | —NH$_2$ | 1 |
| 3-61 | H | 4-FPh | —NH$_2$ | 1 |
| 3-62 | H | 2,4-diClPh | —NH$_2$ | 1 |
| 3-63 | H | 2-Thi | —NH$_2$ | 1 |
| 3-64 | H | 3-Pyr | —NH$_2$ | 1 |
| 3-65 | H | Ph | —NH$_2$ | 0 |
| 3-66 | H | Ph | —NHMe | 0 |
| 3-67 | H | Ph | —NHEt | 0 |
| 3-68 | H | Ph | —NHPr | 0 |
| 3-69 | H | Ph | —NHiPr | 0 |
| 3-70 | H | Ph | —NHBu | 0 |
| 3-71 | H | Ph | —NHiBu | 0 |
| 3-72 | H | Ph | —NHsBu | 0 |
| 3-73 | H | Ph | —NHtBu | 0 |
| 3-74 | H | Ph | —NHPh | 0 |
| 3-75 | H | Ph | —NHBz | 0 |
| 3-76 | H | Ph | —NMe$_2$ | 0 |
| 3-77 | H | Ph | 1-Pyrd | 0 |
| 3-78 | H | Ph | Mor | 0 |
| 3-79 | H | Ph | 1-Piz | 0 |
| 3-80 | H | Ph | 4-Me-1-Piz | 0 |
| 3-81 | H | Ph | 1-Pip | 0 |
| 3-82 | Cl | Ph | —NH$_2$ | 0 |
| 3-83 | Cl | Ph | —NHMe | 0 |
| 3-84 | Cl | Ph | —NHEt | 0 |
| 3-85 | Cl | Ph | —NHPr | 0 |
| 3-86 | Cl | Ph | —NHiPr | 0 |
| 3-87 | Cl | Ph | —NHBu | 0 |
| 3-88 | Cl | Ph | —NHiBu | 0 |
| 3-89 | Cl | Ph | —NHsBu | 0 |
| 3-90 | Cl | Ph | —NHtBu | 0 |
| 3-91 | Cl | Ph | —NHPh | 0 |
| 3-92 | Cl | Ph | —NHBz | 0 |
| 3-93 | Cl | Ph | —NMe$_2$ | 0 |
| 3-94 | Cl | Ph | 1-Pyrd | 0 |
| 3-95 | Cl | Ph | Mor | 0 |
| 3-96 | Cl | Ph | 1-Piz | 0 |

TABLE 3-continued

| Cpd No. | R¹ | R² | R⁵ | n |
|---|---|---|---|---|
| 3-97 | Cl | Ph | 4-Me-1-Piz | 0 |
| 3-98 | Cl | Ph | 1-Pip | 0 |
| 3-99 | Me | Ph | Mor | 0 |
| 3-100 | Et | Ph | —NH₂ | 0 |
| 3-101 | iPr | Ph | —NH₂ | 0 |
| 3-102 | iBu | Ph | —NH₂ | 0 |
| 3-103 | All | Ph | —NH₂ | 0 |
| 3-104 | MeCH=CHCH₂— | Ph | —NH₂ | 0 |
| 3-105 | HC≡C—CH₂ | Ph | —NH₂ | 0 |
| 3-106 | Ph | Ph | —NH₂ | 0 |
| 3-107 | Bz | Ph | —NH₂ | 0 |
| 3-108 | H | H | —NH₂ | 0 |
| 3-109 | H | Me | —NH₂ | 0 |
| 3-110 | H | Et | —NH₂ | 0 |
| 3-111 | H | Pr | —NH₂ | 0 |
| 3-112 | H | iPr | —NH₂ | 0 |
| 3-113 | H | Bu | —NH₂ | 0 |
| 3-114 | H | iBu | —NH₂ | 0 |
| 3-115 | H | sBu | —NH₂ | 0 |
| 3-116 | H | tBu | —NH₂ | 0 |
| 3-117 | Cl | Me | —NH₂ | 0 |
| 3-118 | H | 4-ClPh | —NH₂ | 0 |
| 3-119 | H | 3-ClPh | —NH₂ | 0 |
| 3-120 | H | 4-NO₂Ph | —NH₂ | 0 |
| 3-121 | H | 4-MeOPh | —NH₂ | 0 |
| 3-122 | H | 3-MeOPh | —NH₂ | 0 |
| 3-123 | H | 2-MeOPh | —NH₂ | 0 |
| 3-124 | H | 4-HOPh | —NH₂ | 0 |
| 3-125 | H | 4-FPh | —NH₂ | 0 |
| 3-126 | H | 2,4-diClPh | —NH₂ | 0 |
| 3-127 | H | 2-Thi | —NH₂ | 0 |
| 3-128 | H | 3-Pyr | —NH₂ | 0 |

TABLE 4

| Cpd. No. | R⁶ | R⁷ | R⁸ | R⁹ | R⁵ | n |
|---|---|---|---|---|---|---|
| 4-1 | H | H | H | H | —NH₂ | 1 |
| 4-2 | H | H | H | H | —NHMe | 1 |
| 4-3 | H | H | H | H | —NHEt | 1 |
| 4-4 | H | H | H | H | —NHPr | 1 |
| 4-5 | H | H | H | H | —NHiPr | 1 |
| 4-6 | H | H | H | H | —NHBu | 1 |
| 4-7 | H | H | H | H | —NHiBu | 1 |
| 4-8 | H | H | H | H | —NHsBu | 1 |
| 4-9 | H | H | H | H | —NHtBu | 1 |
| 4-10 | H | H | H | H | —NHPh | 1 |
| 4-11 | H | H | H | H | —NHBz | 1 |
| 4-12 | H | H | H | H | —NMe₂ | 1 |
| 4-13 | H | H | H | H | 1-Pyrd | 1 |
| 4-14 | H | H | H | H | Mor | 1 |
| 4-15 | H | H | H | H | 1-Piz | 1 |
| 4-16 | H | H | H | H | 4-Me-1-Piz | 1 |
| 4-17 | H | H | H | H | 1-Pip | 1 |
| 4-18 | H | Cl | H | H | —NHMe | 1 |
| 4-19 | H | Cl | H | H | —NHEt | 1 |
| 4-20 | H | Cl | H | H | —NHPr | 1 |
| 4-21 | H | Cl | H | H | —NHiPr | 1 |
| 4-22 | H | Cl | H | H | —NHBu | 1 |
| 4-23 | H | Cl | H | H | —NHiBu | 1 |
| 4-24 | H | Cl | H | H | —NHsBu | 1 |
| 4-25 | H | Cl | H | H | —NHtBu | 1 |
| 4-26 | H | Cl | H | H | —NHPh | 1 |
| 4-27 | H | Cl | H | H | —NHBz | 1 |
| 4-28 | H | Cl | H | H | —NMe₂ | 1 |
| 4-29 | H | Cl | H | H | 1-Pyrd | 1 |
| 4-30 | H | Cl | H | H | Mor | 1 |
| 4-31 | H | Cl | H | H | 1-Piz | 1 |
| 4-32 | H | Cl | H | H | 4-Me-1-Piz | 1 |
| 4-33 | H | Cl | H | H | 1-Pip | 1 |
| 4-34 | H | Cl | H | H | —NH₂ | 1 |
| 4-35 | H | H | H | Me | —NH₂ | 1 |
| 4-36 | H | —NH₂ | H | H | —NH₂ | 1 |
| 4-37 | H | —NHAc | H | H | —NH₂ | 1 |
| 4-38 | H | —OMe | H | H | —NH₂ | 1 |
| 4-39 | H | H | H | H | —NHPh | 0 |
| 4-40 | H | H | H | H | —NHBz | 0 |
| 4-41 | H | H | H | H | —NMe₂ | 0 |

TABLE 4-continued

| Cpd. No. | R⁶ | R⁷ | R⁸ | R⁹ | R⁵ | n |
|---|---|---|---|---|---|---|
| 4-42 | H | H | H | H | 1-Pyrd | 0 |
| 4-43 | H | H | H | H | Mor | 0 |
| 4-44 | H | H | H | H | 1-Piz | 0 |
| 4-45 | H | H | H | H | 4-Me-1-Piz | 0 |
| 4-46 | H | H | H | H | 1-Pip | 0 |
| 4-47 | H | Cl | H | H | —NMe₂ | 0 |
| 4-48 | H | Cl | H | H | —N(Me)Et | 0 |
| 4-49 | H | Cl | H | H | —N(Me)Pr | 0 |
| 4-50 | H | Cl | H | H | —NHPh | 0 |
| 4-51 | H | Cl | H | H | —NHBz | 0 |
| 4-52 | H | Cl | H | H | —NEt₂ | 0 |
| 4-53 | H | Cl | H | H | 1-Pyrd | 0 |
| 4-54 | H | Cl | H | H | Mor | 0 |
| 4-55 | H | Cl | H | H | 1-Piz | 0 |
| 4-56 | H | Cl | H | H | 4-Me-1-Piz | 0 |
| 4-57 | H | Cl | H | H | 1-Pip | 0 |
| 4-58 | H | H | Cl | H | —NH₂ | 0 |
| 4-59 | H | H | H | Me | —NH₂ | 0 |
| 4-60 | H | —NH₂ | H | H | —NH₂ | 0 |
| 4-61 | H | —NHAc | H | H | —NH₂ | 0 |
| 4-62 | H | —OMe | H | H | —NH₂ | 0 |
| 4-63 | H | F | H | H | —NH₂ | 1 |
| 4-64 | H | Br | H | H | —NH₂ | 1 |
| 4-65 | H | Me | H | H | —NH₂ | 1 |
| 4-66 | H | Pr | H | H | —NH₂ | 1 |
| 4-67 | H | iBu | H | H | —NH₂ | 1 |
| 4-68 | H | —OPr | H | H | —NH₂ | 1 |
| 4-69 | H | —OiBu | H | H | —NH₂ | 1 |

Of the compounds listed above, the following are particularly preferred, that is to say Compounds No. 1-13, 1-33, 1-34, 1-35, 1-37, 1-38, 1-39, 1-41, 1-45, 1-62, 1-100, 2-34, 3-14, 3-15, 3-16, 3-31, 3-32, 3-33, 3-55, 3-57, 3-58, 3-59, 3-61, 3-62, 3-78, 3-95, 3-96, 3-97, 3-98, 3-99, 3-118, 3-119, 3-121, 3-122, 3-123, 3-125, 3-126, 4-1, 4-14, 4-14, 4-15, 4-16, 4-17, 4-30, 4-31, 4-32, 4-33, 4-34, 4-43, 4-44, 4-45, 4-46, 4-54, 4-55, 4-56 and 4-57, and the following are the most preferred compounds:

1-13. 2-(2-Hydroxy-3-morpholinopropyl)-4-methyl-5-phenyl-3-isoxazolone;

3-55. 3-(3-Carbamoyloxy-2-hydroxypropoxy)-5-(m-chloropheny)isoxazole;

3-78. 3-(2-Hydroxy-3-morpholinopropoxy)-5-phenylisoxazole;

3-99. 3-(2-Hydroxy-3-morpholinopropoxy)-4-methyl-5-phenylisoxazole;

4-34. 3-(3-Carbamoyloxy-2-hydroxypropoxy)-5-chloro-1,2-benzisoxazole;

and pharmaceutically acceptable salts thereof, especially the hydrochlorides.

The compounds of the present invention may be prepared by a variety of processes, each well known in themselves. In general terms, the process of the present invention may be represented as comprising the steps:

(i) reacting a compound of formula (III):

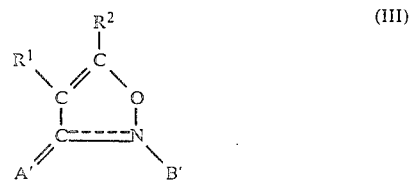

[in which: either
(a) the dotted line (==) represents a single bond;
    A' = represents a oxygen atom; and
    B' represents a group of formula (IV):

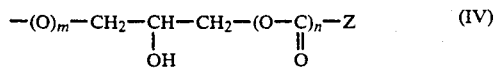 (IV)

in which m is 0 and n is 0 or 1; or
(b) the dotted line (≡) represents a double bond;
  A'=represents said group of formula (IV) in which m is 1 and n is 0 or 1; and
  B' is absent;
Z represents a leaving group;
q and R¹ and R² are as defined above]
with an amine of formula (V):

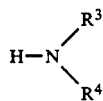 (V)

(in which R³ and R⁴ are as defined above);
and, if necessary, salifying the resulting product.

In more detail, preferred processes for preparing the compounds of the present invention are illustrated below in the following Methods A to D.

Method A:

Compounds of formula (I) in which n is 0, A represents an oxygen atom and B represents said group of formula (II), that is to say compounds of formula (Ia), can be prepared by reacting a compound of formula (VI):

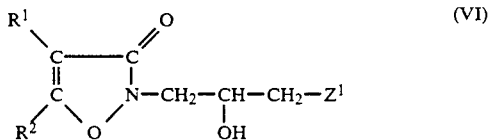 (VI)

(in which R¹ and R² are as defined above and Z¹ represents a halogen atom, for example a chlorine, bromine or iodine atom) with an amine of formula (V), defined above, to give the compound of formula (Ia):

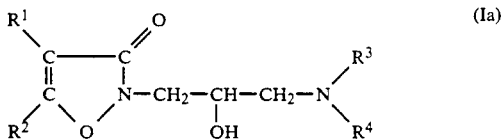 (Ia)

(in which R¹, R², R³ and R⁴ are as defined above).

This reaction may be carried out by condensing the 3-isoxazolone derivative of formula (VI) with an amine of formula (V) in the presence of a base. The nature of the amine of formula (V) will, of course, depend on the nature of the compound which it is desired to prepare. Examples of such compounds include: ammonia, methylamine, ethylamine, propylamine, isopropylamine, butylamine, isobutylamine, sec-butylamine, t-butylamine, dimethylamine, diethylamine, phenylamine, benzylamine, morpholine, piperazine, 1-methylpiperazine, pyrrolidine and piperidine.

The reaction is carried out in the presence of a base, the nature of which is not critical, provided that it has no adverse effect on other parts of the molecule. Examples of suitable bases include: alkali metal hydrides, such as sodium hydride; alkali metal hydroxides, such as sodium hydroxide or potassium hydroxide; alkali metal alkoxides, such as potassium methoxide or sodium ethoxide; and alkali metal carbonates, such as sodium carbonate or potassium carbonate. The reaction is also preferably effected in an inert solvent. There is no particular restriction on the nature of the solvent to be employed, provided that it has no adverse effect on the reaction or on the reagents involved. Examples of suitable solvents include: alcohols, such as methanol, ethanol, propanol, isopropanol and butanol; aromatic hydrocarbons, such as benzene, toluene or xylene; ketones, such as acetone, methyl butyl ketone or methyl amyl ketone; and halogenated hydrocarbons, which may be aliphatic or aromatic, such as tetrachloroethane, chlorobenzene or dichlorobenzene.

The reaction can take place over a wide range of temperatures, and the precise reaction temperature is not critical to the invention. In general, we find it convenient to carry out the reaction at a temperature from 0° C. to 150° C., more preferably from 20° C. to 130° C. The time required for the reaction may also vary widely, depending on many factors, notably the reaction temperature and the nature of the reagents. However, provided that the reaction is effected under the preferred conditions outlined above, a period of from 1 to 4 hours will usually suffice.

The 3-isoxazolone derivative of formula (VI) used as the starting material in this process can be prepared, for example, by the method described in Japanese Patent Provisional Publication No. Sho. 55-83766, the disclosure of which is incorporated herein by reference.

Method B:

Compounds of formula (I) in which n is 1, A=represents a hydrogen atom and said group of formula (II), defined above, and B is absent, that is to say compounds of formula (Ib), can be prepared by reacting, in a first step, an oxirane compound of formula (VII):

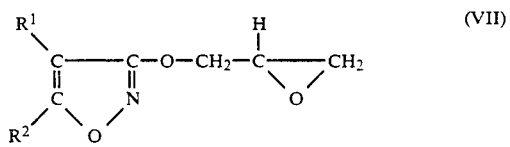 (VII)

(in which R¹ and R² are as defined above) with an alkali to prepare the dihydroxy compound of formula (VIII):

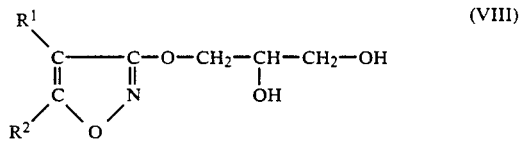 (VIII)

(in which R¹ and R² are as defined above), then, in a second step, reacting said compound of formula (VIII) with phosgene or a halocarbonate ester in the presence of a tertiary amine, and then, in a third step, reacting the resulting carbonate with an amine of formula (V), to give a compound of formula (Ib):

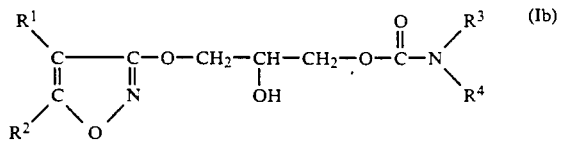 (Ib)

(in which $R^1$, $R^2$, $R^3$ and $R^4$ are as defined above).

In the first step, the reaction for preparing the dihydroxy compound of formula (VIII) is carried out by heating the oxirane compound of formula (VII) in an alkali, preferably in an aqueous solution of an alkali metal carbonate or an alkali metal hydroxide and in the presence of an organic solvent. There is no particular restriction on the nature of the solvent to be employed, provided that it has no adverse effect on the reaction or on the reagents involved. Examples of suitable solvents include: nitriles, such as acetonitrile; alcohols, such as methanol or ethanol; ketones, such as acetone or methyl ethyl ketone; amides, especially fatty acid amides, such as dimethylformamide or dimethylacetamide; and sulfoxides, such as dimethyl sulfoxide. The reagent empoyed in this reaction is an alkali metal carbonate (such as potassium carbonate or sodium carbonate) or an alkali metal hydroxide (such as potassium hydroxide or sodium hydroxide). The reaction can take place over a wide range of temperatures, and the precise reaction temperature is not critical to the invention. In general, we find it convenient to carry out the reaction at around the reflux temperature of the reaction mixture. The time required for the reaction may also vary widely, depending on many factors, notably the reaction temperature and the nature of the reagents. However, provided that the reaction is effected under the preferred conditions outlined above, a period of from 30 minutes to 5 hours will usually suffice.

After the reaction is complete, the dihydroxy compound of formula (VIII) can be recovered from the reaction mixture by conventional means. Thus, in one suitable recovery process, the reaction mixture, if required, is mixed with an aqueous solution of sodium chloride for salting-out; and is then extracted with an organic solvent; the organic layer is washed and dried, and the solvent is removed by distillation by evaporation under reduced pressure, to give the desired compound. This compound may, if required, be further purified by such conventional techniques as, for example, recrystallization or the various chromatography techniques, notably column chromatography.

The second step of the reaction is effected in two stages.

The first of these stages consists of the reaction of the dihydroxy compound of formula (VIII) with phosgene or a halocarbonate ester, followed by the addition of a tertiary amine to the carbonate ester intermediate. The reaction is normally effected in the presence of an organic solvent. There is no particular restriction on the nature of the solvent to be employed, provided that it has no adverse effect on the reaction or on the reagents involved. Examples of suitable solvents include: ethers, such as tetrahydrofuran or dioxane; and aromatic hydrocarbons, such as benzene or toluene. A suitable halocarbonate ester is, for example, trichloromethyl chloroformate, and a suitable tertiary amine is, for example, triethylamine, dimethylaniline or pyridine. The reaction can take place over a wide range of temperatures, and the precise reaction temperature is not critical to the invention. In general, we find it convenient to carry out the reaction at around room temperature. The time required for the reaction may also vary widely, depending on many factors, notably the reaction temperature and the nature of the reagents. However, provided that the reaction is effected under the preferred conditions outlined above, a period of from 1 to 6 hours will usually suffice.

After completion of the reaction, insoluble materials are removed by filtration, and the filtrate may then be subjected to the reaction in the subsequent stage.

The reaction in the second stage consists of the reaction of an amine of formula (V) with the carbonate intermediate obtained in the preceding stage. Suitable amines of formula (V) which may be employed in this stage include those referred to in connection with Method A, although, of course, the amine chosen will depend on the nature of the desired final product. The reaction can take place over a wide range of temperatures, and the precise reaction temperature is not critical to the invention. The time required for the reaction may also vary widely, depending on many factors, notably the reaction temperature and the nature of the reagents. In general, we find it convenient to carry out the reaction at around room temperature for a period of from 1 to 5 hours, and then under reflux of the solvent employed for a further period of from 1 to 5 hours. In order to complete the reaction, if required, the reaction mixture may be concentrated, a further quantity of the amine of formula (V) and an alcohol (such as methanol or ethanol) are added to the residue, and the mixture may be heated under reflux for a period of from 1 to 5 hours.

The oxirane compound of formula (VII) used as the starting material in the above reactions can be prepared from a 3-hydroxyisoxazole compound and an epihalohydrin according to the method described in Japanese Patent Provisional Publication No. Sho. 52-31070, the disclosure of which is incorporated herein by reference.

Method C:

Compounds of formula (I) in which n is 0, A = represents a hydrogen atom and said group of formula (II), defined above, and B is absent, that is to say compounds of formula (Ic), can be prepared by reacting, in a first step, an oxirane compound of formula (VII), as defined above in Method B, with an amine of formula (V), as defined above in Method A, to give the compound of formula (Ic):

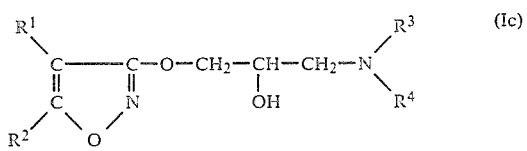

(in which $R^1$, $R^2$, $R^3$ and $R^4$ are as defined above).

This reaction is, in essence, the same as that described above in the second stage of the second step of Method B, and may be carried out employing the same reagents and starting materials.

Method D:

Compounds of formula (I) in which n is 1, A represents an oxygen atom and B represents said group of formula (II), that is to say compounds of formula (Id), can be prepared by reacting a compound of formula (IX):

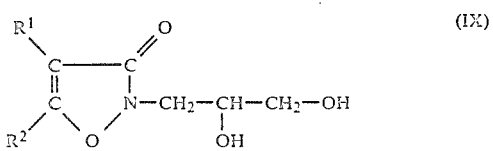

(in which R¹ and R² are defined above) with phosgene or a halocarbonate ester in the presence of a tertiary amine, and then, in a further step, reacting the resulting carbonate with an amine of formula (V), to give the compound of formula (Id):

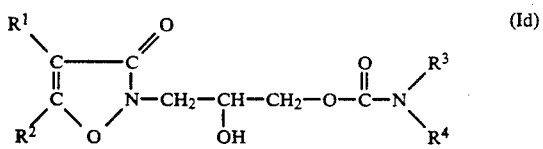

(in which $R^1$, $R^2$, $R^3$ and $R^4$ are as defined above). These reactions are essentially the same as those in the second step of Method B, and may be carried out using the same reagents and reaction conditions.

The dihydroxy compound of formula (IX) used as the starting material in the above reaction can be prepared from a 3-hydroxyisoxazole compound and an epihalohydrin according to the method described in Japanese Patent Provisional Publication No. Sho. 55-83766, the disclosure of which is incorporated herein by reference.

After completion of any of the above reactions, the desired compound can be recovered from the reaction mixture by conventional means. For instance, if the desired compound has crystallized out from the reaction mixture, it may be collected by filtration, or, if the desired compound is in a liquid state, the solvent may be removed by distillation from the reaction mixture and the residue dissolved in a solvent which is slightly soluble in water; the resulting solution may then be washed with an acid and water, in that order, and the desired compound can then be obtained by evaporation of the solvent. The product may, if required, be further purified by various conventional techniques such as, for example, recrystallization, vacuum distillation or the various chromatography techniques, such as column chromatography or preparative thin layer chromatography.

As shown in the pharmacological activity and toxicity tests described in the Experiments given hereafter, the compounds of the present invention have an excellent ability to counter some symptoms elicited by cerebral ischemia and have a centrally-acting muscle relaxant activity, combined with a low toxicity. Moreover, the compounds of the present invention do not induce much drowsiness, which makes their administration less difficult than that of other similar drugs.

Typically the compounds of the present invention are rapidly absorbed after oral administration, intraduodenal or intraperitoneal administration. They are expected to be particularly useful as centrally acting muscle relaxants for cerebral stroke infarction sequelae and cerebrotraumatic sequelae, and for spasrigido hemiplegia, post-operative sequelae (including tumor of the brain and spinal cord), traumatic sequelae (spinal cord injury, cephalic trauma), amyotrophic lateral sclerosis, cerebral palsy, spinocerebellar degeneration, disorders of the spinal cord vessel, SMON (sub-acute myelo-optic neuropathy), caisson disease, spastic paralysis due to any other spinal cord disease, and increased myotony such as systemic cramp or shoulder stiffness. They are also expected to be useful as cerebro-active drugs for the treatment of the acute and chronic phases of cerebral stroke infarction or for the postoperative treatment of patients with a cerebral tumor, a head injury, or the like.

The compounds of the present invention may therefore be used in the treatment of such disorders, and, for this purpose, may be formulated as conventional pharmaceutical preparations, as is well known in the art. Thus, the compounds may be administered orally, e.g. in the form of tablets, capsules, granules, powders, syrups, or other such well known forms, or parenterally, e.g. by injections, suppositories, etc.

These pharmaceutical preparations can be prepared by conventional means and may contain known adjuvants of a type commonly used in this field, for example vehicles, binders, disintegrators, lubricants, correctives, etc. depending upon the intended use and form of the preparation. The dose will depend upon the condition, age, and body weight of the patient as well as upon the nature and severity of the disorder to be treated, but in the case of oral administration to an adult human patient, we would normally suggest a total daily dose of from 5 mg to 50 mg, which may be administered in a single dose or in divided doses, e.g. from one to three times a day for a total dosage of 5-150 mg per day, for all uses described above.

In general, the compounds of formula (Ia) do not induce much drowsiness, have low toxicity and have a centrally-acting muscle relaxant activity. Typically the compounds are rapidly absorbed after oral administration, intraduodenal or intraperitoneal administration and manifest the muscle relaxant effect. They are expected to be particularly useful as centrally-acting muscle relaxants for cerebral apoplectic sequelae and cephalo-traumatic sequelae, and for spastic spinal paralysis, cervicospinal disease post-operative sequelae (including tumor of the brain and spinal cord), traumatic sequelae spinal cord injury, cephalic trauma), amyotrophic lateral sclerosis, cerebral palsy, spinocerebellar degeneration, disorders of the spinal cord vessel, SMON (subacute myelo-optic neuropathy), caisson disease, spasmic paralysis due to any other spinal cord disease, and increased myotony such as systemic cramp or shoulder stiffness.

As noted above administration modes include oral administration by tablets, capsules, granules, powders and syrups, and parenteral administration by injections and suppositories.

And as can be seen from the results described below, the compounds of the present invention have a so-called cerebroprotective effect, which improved ischemia-induced neurological symptoms caused by ligation of the bilateral common carotid arteries, without inducing sleep and with an extremely low toxicity. It has been found that the compounds of the present invention are absorbed very well by the oral route, and, furthermore, since the hydrochloride is soluble in water, it is clinically possible for it to be administered intravenously or orally, as required. Although the compounds of the present invention are known, their known activity could not have been predicted that they would be useful as cerebro-active drugs for the treatment of the acute and chronic phases of cerebral stroke infraction or for the post-operative treatment of patients with cerebral tumor, a head injury, or the like.

The preparation of the compounds of the invention is further illustrated by the following Examples 1 to 20, whilst their use for the preparation of pharmaceutical formulations is illustrated in Examples 21 to 29. Preparation of certain intermediates for use in the preparation of the compounds of the present invention is then illustrated in the subsequent Preparations. (In these Examples, all sieve sizes are Tyler standard mesh.) The subsequent Experiments illustrate the biological activity of the compounds of the present invention.

EXAMPLE 1

2-(2-Hydroxy-3-morpholinopropyl)-4-methyl-5-phenyl-3-isoxazolone 1.55 g (17.9 mmoles) of morpholine and 2.46 g (17.9 mmoles) of anhydrous potassium carbonate powder were added to a solution of 4.00 g (14.9 mmoles) of 2-(3-chloro-2-hydroxypropyl)-4-methyl-5-phenyl-3-isoxazolone in 50 ml of ethanol, and the mixture was heated under reflux for 4 hours. At the end of this time, the reaction mixture was cooled by allowing it to stand, and then insoluble materials were removed by filtration. The filtrate was then concentrated by evaporation under reduced pressure, and the residue was purified by column chromatography through silica gel, using ethyl acetate containing 5% by volume methanol as the eluent, to give 4.21 g (yield 83.5%) of the title compound as a colorless syrupy substance.

$n_D^{24} = 1.5740$.

Infrared Absorption Spectrum (CHCl$_3$) $\nu_{max}$ cm$^{-1}$: 3400 (OH), 1660 (shoulder), 1645 (C=O).

Nuclear Magnetic Resonance Spectrum (CDCl$_3$) δ ppm: 2.10 (3H, singlet); 2.23–2.83 (2H×3, multiplet); 3.70 (2H×2, triplet, J=4.5 Hz); 3.93 (1H, broad singlet); 4.10 (2H, doublet, J=3.0 Hz); 3.80–4.30 (1H, multiplet); 7.26–7.83 (5H, multiplet).

EXAMPLE 2

2-(2-Hydroxy-3-morpholinopropyl)-4-methyl-5-phenyl-3-isoxazolone hydrochloride 2.00 ml of a 4N solution of hydrogen chloride in dioxane were added to a solution of 2.50 g (7.4 mmoles) of 2-(2-hydroxy-3-morpholinopropyl)-4-methyl-5-phenyl-3-isoxazolone (prepared as described in Example 1) in 25 ml of ethanol, and the mixture was stirred at room temperature for 3 hours. At the end of this time, the crystals which deposited were collected by filtration, washed with 10 ml of isopropanol, and recrystallized from ethanol, to give 2.30 g (yield 87.7%) of the title compound as a colorless powder, melting at 130°–133° C.

Infrared Absorption Spectrum (KBr) $\nu_{max}$ cm$^{-1}$: 3700–3100 (—OH), 1646 (C=O).

Nuclear Magnetic Resonance Spectrum (D$_2$O) δ ppm: 2.40 (3H, singlet); 3.60–4.10 (2H×3, multiplet); 4.44 (2H, doublet, J=4.5 Hz); 4.53 (2H×2, triplet, J=4.5 Hz); 4.83–5.23 (1H, multiplet); 7.86–8.26 (5H, multiplet).

EXAMPLE 3

3-(3-Carbamoyloxy-2-hydroxypropoxy)-5-chloro-1,2-benzisoxazole

3(a)

5-Chloro-3-(2,3-dihydroxypropoxy)-1,2-benzisoxazole 256 ml of a 10% w/v aqueous solution of potassium carbonate were added to a suspension of 21.0 g (92.7 mmoles) of 5-chloro-3-(2,3-epoxypropoxy)-1,2-benzisoxazole (prepared according to the method described in Japanese Patent Provisional Publication No. Sho. 52-31070) in 100 ml of acetonitrile, and the mixture was then heated under reflux for 3 hours. At the end of this time, the reaction mixture was cooled by allowing it to stand, and then 500 ml of water were added. The reaction mixture was then extracted with 1 liter of ethyl acetate. The organic extract was dried over anhydrous magnesium sulfate, the desiccant was removed by filtration, and the solvent was removed by distillation to give a solid residue. This was then recrystallized from a mixture of ethyl acetate and diethyl ether, to give 16.7 g (yield 74.2%) of the title compound as a colorless amorphous powder, melting at 61°–62° C.

Infrared Absorption Spectrum (KBr) $\nu_{max}$ cm$^{-1}$: 3410 (OH), 1600, 1539 (C=N, Ar).

Nuclear Magnetic Resonance Spectrum (CDCl$_3$) δ ppm: 2.90 (1H×2, broad singlet); 3.60–4.00 (2H, multiplet); 4.00–4.40 (1H, multiplet); 4.52 (2H, doublet, J=4.5 Hz); 7.20–7.70 (3H, multiplet).

3(b)

3-(3-Carbamoyloxy-2-hydroxypropoxy)-5-chloro-1,2-benzisoxazole 5.9 g (29.8 mmoles) of trichloromethyl chloroformate were added dropwise at 10° C. to a solution of 16.0 g (55.8 mmoles) of 5-chloro-3-(2,3-dihydroxypropoxy)-1,2-benzisoxazole [prepared as described in step (a) above] in 500 ml of dry benzene; the mixture was then stirred at the same temperature for 30 minutes, after which 6.1 g (60.3 mmoles) of triethylamine were added dropwise at 10°–15° C. The mixture was then stirred for a further 1 hour at 5°–10° C., after which insoluble materials were removed by filtration and washed with 100 ml of dry benzene. The filtrate and washings were combined, and cooled to 10° C., and then 38.0 ml (304.0 mmoles) of 28% v/v aqueous ammonia were added thereto at one time. The mixture was then stirred at room temperature for 2 hours, after which it was heated under reflux for an additional 2 hours. The reaction mixture was then concentrated by evaporation under reduced pressure, and 38.0 ml (304.0 mmoles) of 28% v/v aqueous ammonia and 200 ml of ethanol were added to the residue. The resulting mixture was then heated under reflux for a further 2 hours. At the end of this time, the reaction mixture was cooled by allowing it to stand, and the cooled mixture was then concentrated by evaporation under reduced pressure. The residue was purified by column chromatography through silica gel, eluted with a 1:2 by volume mixture of benzene and ethyl acetate, followed by recrystallization from ethyl acetate, to give 11.6 g (72.5%) of the title compound as a colorless amorphous powder, melting at 123°–124° C.

Infrared Absorption Spectrum (KBr) $\nu_{max}$ cm$^{-1}$: 3395, 3340, 3280, 3200 (NH$_2$, OH), 1730 (C=O).

Nuclear Magnetic Resonance Spectrum (hexadeuterated dimethyl sulfoxide) δ ppm: 3.96–4.50 (2H+2H+1H, multiplet) 5.34 (1H, doublet, J=4.5 Hz); 6.50 (2H, broad singlet); 7.60–7.90 (3H, multiplet).

EXAMPLE 4

3-(3-Carbamoyloxy-2-hydroxypropoxy)-5-(m-chlorophenyl)isoxazole

4(a)

5-(m-Chlorophenyl)-3-(2,3-dihydroxypropoxy)isoxazole 100 ml (72.3 mmoles) of a 10% w/v aqueous solution of potassium carbonate were added to a solution of 15.0 g (59.6 mmoles) of 5-(m-chlorophenyl)-3-(2,3-epoxypropoxy)isoxazole (prepared as described in Preparation 2) in 50 ml of acetonitrile, and the mixture was heated under reflux for 3 hours. At the end of this time, the reaction mixture was cooled by allowing it to stand, and then 400 ml of a 10% w/v aqueous solution of sodium chloride were added thereto, and the mixture was extracted twice, each time with 400 ml of ethyl acetate. The combined organic extracts were dried over anhydrous magnesium sulfate, and the solvent was removed by distillation under reduced pressure. The resulting residue was then purified by column chromatography through silica gel, eluted with a 1:2 by volume mixture of benzene and ethyl acetate, to give 13.2 g (yield 82.5%) of the title compound as a colorless amorphous powder, melting at 92°–93° C.

Infrared Absorption Spectrum (KBr) $v_{max}$ cm$^{-1}$: 3370 (OH), 3105 (Hetero-H).

Nuclear Magnetic Resonance Spectrum (hexadeuterated dimethyl sulfoxide) δ ppm: 3.30–3.70 (2H, multiplet); 3.70–4.10 (1H, multiplet); 4.00–4.50 (2H, multiplet); 4.56 (1H, triplet, J=4.5 Hz); 5.06 (1H, doublet, J=4.5 Hz); 6.93 (1H, singlet); 7.43–8.06 (4H, multiplet).

4(b)
3-(3-Carbamoyloxy-2-hydroxypropoxy)-5-(m-chlorophenyl)isoxazole

A solution of 10.0 g (37.0 mmoles) of 5-(m-chlorophenyl)-3-(2,3-dihydroxypropoxy)isoxazole [prepared as described in step (a) above] in 300 ml of dry tetrahydrofuran was cooled to 5° C., and then 3.96 g (20.0 mmoles) of trichloromethyl chloroformate were added dropwise to the mixture. The mixture was then stirred at 5°–6° C. for 30 minutes. At the end of this time, 4.04 g (40.0 mmoles) of triethylamine were added dropwise to the mixture at 5°–10° C., and the mixture was stirred at 3°–5° C. for 1 hour. 50 ml (400.0 mmoles) of 28% v/v aqueous ammonia were then added at one time, and the mixture was stirred at room temperature for a further 18 hours. The reaction mixture was then concentrated by evaporation under reduced pressure, and the resulting residue was diluted with 400 ml of ethyl acetate. The mixture was then washed with 400 ml of a 10% w/v aqueous solution of sodium chloride. The organic layer was dried over anhydrous magnesium sulfate, the desiccant was removed by filtration, and the solvent was removed by distillation under reduced pressure to give a solid residue. This solid residue was recrystallized from ethyl acetate, to give 8.30 g (yield 72.1%) of the title compound as colorless scales, melting at 149°–150° C.

Infrared Absorption Spectrum (KBr) $v_{max}$ cm$^{-1}$: 3430, 3320, 3245 (NH$_2$, OH), 3120 (Hetero-H), 1683 (C=O).

Nuclear Magnetic Resonance Spectrum (hexadeuterated dimethyl sulfoxide) δ ppm: 3.86–4.33 (2H+2H+1H, multiplet) 5.32 (1H, doublet, J=4.5 Hz); 6.50 (2H, broad singlet); 6.93 (1H, singlet); 7.50–8.00 (4H, multiplet).

EXAMPLE 5
3-(2-Hydroxy-3-morpholinopropoxy)-4-methyl-5-phenylisoxazole 1.40 g of morpholine was added to a solution of 3.00 g of 3-(2,3-epoxypropoxy)-4-methyl-5-phenylisoxazole (prepared as described in Preparation 3) in 50 ml of ethanol, and the mixture was heated under reflux for 3 hours. At the end of this time, the reaction mixture was concentrated by evaporation under reduced pressure, and the resulting solid residue was recrystallized from diethyl ether, to give 3.75 g (yield 90.7%) of the title compound as a colorless powder, melting at 94°–95° C.

Infrared Absorption Spectrum (KBr) $v_{max}$ cm$^{-1}$: 3380 (OH).

Nuclear Magnetic Resonance Spectrum (CDCl$_3$) δ ppm: 2.10 (3H, singlet); 2.30–2.85 (2H×3, multiplet); 2.70–3.40 (1H, broad); 3.71 (2H×2, triplet, J=4.5 Hz); 4.00–4.55 (1H, multiplet); 4.25–4.50 (2H, multiplet); 7.35–7.85 (5H, multiplet).

EXAMPLE 6
3-(2-Hydroxy-3-morpholinopropoxy)-4-methyl-5-phenylisoxazole hydrochloride 2.75 ml of a 4N solution of hydrogen chloride in dioxane were added to a solution of 3.18 g of 3-(2-hydroxy-3-morpholinopropoxy)-4-methyl-5-phenylisozazole (prepared as described in Example 5) in 50 ml of ethanol, and the mixture was stirred at room temperature for 3 hours. At the end of this time, the crystalline substance which deposited was recrystallized from ethanol, to give 3.20 g (yield 90.4%) of the title compound as colorless granules, melting at 189°–191° C. (with decomposition).

Infrared Absorption Spectrum (KBr) $v_{max}$ cm$^{-1}$: 3405 (OH).

Nuclear Magnetic Resonance Spectrum (D$_2$O) δ ppm: 2.30 (3H, singlet); 3.60–4.10 (2H×3, multiplet); 4.50 (2H, doublet, J=4.5 Hz); 4.63 (2H, doublet, J=4.5 Hz); 4.70–5.20 (1H, multiplet); 7.90 (5H, singlet).

EXAMPLES 7 TO 14

Following a procedure similar to that described in Examples 5 and 6, the compounds listed in the following Table 5 were prepared.

TABLE 5

| Example No. | Compound | Melting Point (°C.) |
|---|---|---|
| 7 | 3-(2-Hydroxy-3-morpholinopropoxy)-5-phenylisoxazole | 123–124 |
| 8 | 4-Chloro-3-(2-hydroxy-3-morpholinopropoxy)-5-phenylisoxazole | 75–76 |
| 9 | 5-(p-Chlorophenyl)-3-(2-hydroxy-3-morpholinopropoxy)isoxazole | 114–115 |
| 10 | 3-(2-Hydroxy-3-morpholinopropoxy)-5-phenylisoxazole .HCl | 149–150 |
| 11 | 3-(3-Hexylamino-3-hydroxypropoxy)-5-phenylisoxazole | 115–116 |
| 12 | 5-(m-Chlorophenyl)-3-(2-hydroxy-3-morpholinopropoxy)isoxazole | 76–77 |
| 13 | 5-Chloro-3-(2-hydroxy-3-morpholinopropoxy)-1,2-benzisoxazole | 73–74 |
| 14 | 4-Chloro-3-(2-hydroxy-3-morpholinopropoxy)-5-phenylisoxazole.HCl | 200–202 (with decomp.) |

EXAMPLE 15
2-(3-Carbamoyloxy-2-hydroxypropyl)-5-chloro-1,2-benzisoxazol-3-one 0.40 g of trichloromethyl chloroformate was added to a solution of 1.00 g of 5-chloro-2-(2,3-dihydroxypropyl)-1,2-benzisoxazol-3-one (prepared as disclosed in Japanese Patent Application Kokai No. Sho. 55-83766) in 20 ml of dry tetrahydrofuran and the mixture was then stirred at room temperature for 30 minutes. After this, 0.42 g of triethylamine was added dropwise at 5° C., and the mixture was again stirred at the same temperature for 30 minutes. At the end of this time, 5.0 ml of 28% v/v aqueous ammonia were added, and the mixture was stirred at room temperature for 2 hours. It was then heated under reflux for an additional 3 hours. The reaction mixture was then concentrated by evaporation under reduced pressure, and the residue was dissolved in 100 ml of ethyl acetate, washed with a 10% w/v aqueous solution of sodium chloride, and dried over anhydrous magnesium sulfate. The solvent was then removed by distillation under reduced pressure, and the residue was purified by column chromatography through silica gel, eluted with ethyl acetate, to give 0.75 g (yield 64.1%) of the title compound as a colorless powder, melting at 161°–162° C.

Infrared Absorption Spectrum (KBr) $\nu_{max}$ cm$^{-1}$: 3420, 3320, 3260 (OH, NH$_2$), 1683, 1662 (C=O).

Nuclear Magnetic Resonance Spectrum (hexadeuterated dimethyl sulfoxide) δ ppm: 3.86–4.46 (5H, broad); 5.31 (1H, doublet, J=4.5 Hz); 6.50 (2H, singlet); 7.46–7.90 (3H, multiplet).

EXAMPLES 16 TO 18

Following a procedure similar to that described in Example 15, the compounds listed in the following Table 6 were prepared.

TABLE 6

| Example No. | Compound | Melting Point (°C.) |
|---|---|---|
| 16 | 2-(3-Carbamoyloxy-2-hydroxypropyl)-5-phenyl-3-isoxazolone | 183–184 |
| 17 | 2-(3-Carbamoyloxy-2-hydroxypropyl)-4-chloro-5-phenyl-3-isoxazolone | 114–115 |
| 18 | 2-(3-Carbamoyloxy-2-hydroxypropyl)-5-(m-chlorophenyl)-3-isoxazolone | 138–140 |

EXAMPLE 19

3-(2-Hydroxy-3-morpholinopropoxy)-5-phenylisoxazole 17.6 g of morpholine were added to a solution of 40.0 g of 3-(2,3-epoxypropoxy)-5-phenylisoxazole (prepared as described in Preparation 4) in 400 ml of ethanol, and the mixture was heated under reflux for 5 hours. At the end of this time, the reaction mixture was concentrated by evaporation under reduced pressure, and the resulting solid residue was recrystallized from ethyl acetate, to give 50.0 g (yield 89.2%) of the title compound as colorless columnar crystals, melting at 123°–124° C.

Infrared Absorption Spectrum (KBr) $\nu_{max}$ cm$^{-1}$: 3190, 1624, 1511, 1440.

Nuclear Magnetic Resonance Spectrum (CDCl$_3$) δ ppm: 2.30–2.85 (2H×3, multiplet); 3.20–3.70 (1H, broad); 3.73 (2H×2, triplet, J=4.5 Hz); 3.90–4.55 (1H, multiplet); 4.15–4.50 (2H, multiplet); 6.18 (1H, singlet); 7.35–7.85 (5H, multiplet).

EXAMPLE 20

3-(2-Hydroxy-3-morpholinopropoxy)-5-phenylisoxazole hydrochloride 5.0 ml of a 4N solution of hydrogen chloride in dioxane were added to a solution of 5.00 g of 3-(2-hydroxy-3-morpholinopropoxy)-5-phenylisoxazole (prepared as described in Example 19) in 200 ml of ethyl acetate, and the mixture was stirred at room temperature for 10 minutes. At the end of this time, the reaction mixture was concentrated by evaporation under reduced pressure, and the resulting solid residue was recrystallized from ethyl acetate, to give 5.21 g (yield 93.0%) of the title compound as a colorless powder, melting at 149°–150° C.

Infrared Absorption Spectrum (KBr) $\nu_{max}$ cm$^{-1}$: 3215, 1625, 1513, 1461.

Nuclear Magnetic Resonance Spectrum (D$_2$O) δ ppm: 3.66–4.13 (2H×3, multiplet); 4.50 (2H×2, triplet, J=4.5 Hz); 4.69 (2H, doublet, J=4.5 Hz); 4.80–5.20 (1H, multiplet); 6.83 (1H, singlet); 7.80–8.30 (5H, multiplet).

EXAMPLE 21

Capsules

The following powders were mixed:

| | |
|---|---|
| 2-(2-Hydroxy-3-morpholinopropyl)-4-methyl-5-phenyl-3-isoxazolone hydrochloride (compound of Example 2) | 25.0 mg |
| Lactose | 153.6 mg |
| Corn starch | 100.0 mg |
| Magnesium stearate | 1.4 mg |
| Total | 280.0 mg | and then passed through a 60 mesh sieve. 280 mg of the resulting powder were packed into a No. 3 gelatin capsule.

EXAMPLE 22

Capsules

The following powders were mixed:

| | |
|---|---|
| 3-(3-Carbamoyloxy-2-hydroxypropoxy)-5-chloro-1,2-benzisoxazole (The compound of Example 3) | 25.0 mg |
| Lactose | 153.6 mg |
| Corn starch | 100.0 mg |
| Magnesium stearate | 1.4 mg |
| Total | 280.0 mg | and then passed through a 60 mesh sieve. 280 mg of the resulting powder were packed into a No. 3 gelatin capsule.

EXAMPLE 23

Capsules

The following powders were mixed:

| | |
|---|---|
| 3-(2-Hydroxy-3-morpholinopropoxy)-4-methyl-5-phenylisoxazole (The compound of Example 5) | 25.0 mg |
| Lactose | 153.6 mg |
| Corn starch | 100.0 mg |
| Magnesium stearate | 1.4 mg |
| Total | 280.0 mg | and then passed through a 60 mesh sieve. 280 mg of the resulting powder were packed into a No. 3 gelatin capsule.

EXAMPLE 24

Capsules

The following powders were mixed:

| | |
|---|---|
| 3-(3-Carbamoyloxy-2-hydroxypropoxy)-5-(m-chlorophenyl)isoxazole (the compound of Example 4) | 25.0 mg |
| Lactose | 153.6 mg |
| Corn starch | 100.0 mg |

| | |
|---|---|
| Magnesium stearate | 1.4 mg |
| | Total 280.0 mg | and then passed through a 60 mesh sieve. 280 mg of the resulting powder were packed into a No. 3 gelatin capsule.

EXAMPLE 25

Capsules

The following powders were mixed:

| | |
|---|---|
| 2-(3-Carbamoyloxy-2-hydroxypropyl)-5-chlorobenzisoxazolin-3-one (The compound of Example 15) | 25.0 mg |
| Lactose | 153.6 mg |
| Corn starch | 100.0 mg |
| Magnesium stearate | 1.4 mg |
| | Total 280.0 mg | and then passed through a 60 mesh sieve. 280 mg of the resulting powder were packed into a No. 3 gelatin capsule.

EXAMPLE 26

Capsules

The following powders were mixed:

| | |
|---|---|
| 3-(2-Hydroxy-3-morpholinopropoxy)-5-phenylisoxazole hydrochloride (the compound of Example 20) | 25.0 mg |
| Lactose | 153.6 mg |
| Corn starch | 100.0 mg |
| Magnesium stearate | 1.4 mg |
| Total | 280.0 mg | and then passed through a 60 mesh sieve. 280 mg of the resulting powder were packed into a No. 3 gelatin capsule.

EXAMPLE 27

Tablets 120 mg tablets were prepared by conventional tabletting procedures based on the following formulation:

| | |
|---|---|
| 2-(2-Hydroxy-3-morpholinopropyl)-5-phenyl-4-isoxazolin-3-one | 10.0 mg |
| Corn starch | 25.0 mg |
| Lactose | 83.3 mg |
| HPC (Product of Nippon Soda Co., Ltd.) | 1.2 mg |
| Magnesium stearate | 0.5 mg |
| Total | 120.0 mg |

EXAMPLE 28

Capsules

A powder was prepared in accordance with the following formulation, mixed well, and passed through a 60-mesh sieve. 280 mg aliquots of the sieved powder were put into gelatine capsules (No. 3) to give the filled capsules.

| | |
|---|---|
| 2-(2-Hydroxy-3-morpholinopropyl)-5-phenyl-4-isoxazolin-3-one | 25.0 mg |
| Lactose | 153.6 mg |

| | |
|---|---|
| Corn starch | 100.0 mg |
| Magnesium stearate | 1.4 mg |
| | Total 280.0 mg |

EXAMPLE 29

Capsules

A powder was prepared in accordance with the following formulation, mixed well, and passed through a 60-mesh sieve. 280 mg aliquots of the sieved powder were put into gelatine capsules (No. 3) to give the filled capsules.

| | |
|---|---|
| 4-Chloro-2-(2-hydroxy-3-morpholinopropyl)-5-phenyl-4-isoxazolin-3-one | 25.0 mg |
| Lactose | 153.6 mg |
| Corn starch | 100.0 mg |
| Magnesium stearate | 1.4 mg |
| | Total 280.0 mg |

PREPARATION 1

2-(3-Chloro-2-hydroxypropyl)-4-methyl-5-phenyl-3-isoxazolone

A mixture of 6.00 g (34.2 mmoles) of 3-hydroxy-4-methyl-5-phenylisoxazole and 6.33 g (68.4 mmoles) of epichlorohydrin was stirred, whilst heating at 75° C., for 5 hours. At the end of this time, the excess epichlorohydrin was removed by distillation under reduced pressure, and the resulting residue was purified by column chromatography through silica gel, using a 2:1 by volume mixture of cyclohexane and ethyl acetate as eluent, to give 6.51 g (yield 71.1%) of the title compound as a colorless powder, melting at 82°–83° C.

Infrared Absorption Spectrum (KBr) $v_{max}$ cm$^{-1}$: 3265 (OH), 1651, 1637 (C=O).

Nuclear Magnetic Resonance Spectrum (CDCl$_3$) δ ppm: 2.10 (3H, singlet); 3.40–3.83 (2H, multiplet); 4.23 (2H, doublet, J=3.0 Hz); 3.90–4.50 (1H, broad singlet); 4.63 (1H, broad singlet); 7.30–7.83 (5H, multiplet).

PREPARATION 2

5-(m-Chlorophenyl)-3-(2,3-epoxypropoxy)isoxazole 29.6 g (0.153 moles) of sodium methoxide (as a 28% w/v methanolic solution) were added to a solution of 30.0 g (0.153 moles) of 5-(m-chlorophenyl)-3-hydroxyisoxazole in 300 ml of dimethylformamide, and the mixture was stirred at room temperature for 30 minutes. At the end of this time, 41.9 g (0.306 moles) of epibromohydrin were added dropwise, and the mixture was stirred for a further 3 days. The reaction mixture was then concentrated by evaporation under reduced pressure, and the residue was diluted with ethyl acetate. The resulting mixture was washed with 800 ml of a 10% w/v aqueous solution of sodium chloride. The organic layer was then dried over anhydrous magnesium sulfate, the desiccant was removed by filtration, and the solvent was removed by distillation under reduced pressure. The residue was purified by column chromatography through silica gel, eluted with a 2:1 by volume mixture of benzene and ethyl acetate, to give a solid residue, which was recrystallized from diisopropyl ether, to give 23.6 g (yield 73.5%) of the title compound as colorless needles, melting at 86°–87° C.

Infrared Absorption Spectrum (KBr) $\nu_{max}$ cm$^{-1}$: 3120 (Hetero-H), 1620, 1593 (C=N, Ar).

Nuclear Magnetic Resonance Spectrum (CDCl$_3$) δ ppm: 2.72 (1H, AB-doublet of doublets, J=4.5 & 3.0 Hz); 2.88 (1H, AB-doublet of doublets, J=4.5 & 4.5 Hz); 3.26–3.50 (1H, multiplet); 4.18 (1H, AB-doublet of doublets, J=12.0 & 6.0 Hz); 4.58 (1H, AB-doublet of doublets, J=12.0 & 3.0 Hz); 6.20 (1H, singlet); 7.23–7.83 (4H, multiplet).

PREPARATION 3

3-(2,3-Epoxypropoxy)-4-methyl-5-phenylisoxazole 7.32 g of sodium methoxide were added to a solution of 6.00 g of 3-hydroxy-4-methyl-5-phenylisoxazole in 500 ml of dimethylformamide, and the mixture was stirred at room temperature for 10 minutes. 10.4 g of epibromohydrin were then added dropwise at room temperature to the mixture, and the mixture was stirred at room temperature for 48 hours. At the end of this time, the reaction mixture was concentrated by evaporation under reduced pressure, and the residue was purified by column chromatography through silica gel, eluted with a 2:1 by volume mixture of cyclohexane and ethyl acetate, to give 5.60 g of the title compound as colorless cotton-like crystals, melting at 87°–88° C.

Infrared Absorption Spectrum (KBr) $\nu_{max}$ cm$^{-1}$: 1519.

Nuclear Magnetic Resonance Spectrum (CDCl$_3$) δ ppm: 2.10 (3H, singlet); 2.71 (1H, AB-doublet of doublets, J=4.5, 3.0 Hz); 2.86 (1H, AB-doublet of doublets, J=4.5, 4.5 Hz); 3.26–3.53 (1H, multiplet); 4.20 (1H, AB-doublet of doublets, J=12.0, 6.0 Hz); 4.60 (1H, AB-doublet of doublets, J=12.0, 3.0 Hz); 7.20–7.83 (5H, multiplet).

PREPARATION 4

3-(2,3-Epoxypropoxy)-5-phenylisoxazole 10.28 g of anhydrous potassium carbonate and 6.89 g of epichlorohydrin were added to a solution of 10.00 g of 3-hydroxy-5-phenylisoxazole in 50 ml of hexamethylphosphoric triamide, and the mixture was stirred at room temperature for 24 hours. At the end of this time, insoluble materials were removed by filtration from the reaction mixture, and 200 ml of ethyl acetate were added thereto. The mixture was then washed twice, each time with 200 ml of a 10% w/v aqueous solution of sodium chloride. The organic layer was then dried over anhydrous magnesium sulfate, the solvent was removed by distillation under reduced pressure, and the residue was purified by column chromatography through silica gel, eluted with a 4:1 by volume mixture of cyclohexane and ethyl acetate, to give 11.00 g (yield 82%) of the title compound as colorless needles, melting at 98°–99° C.

Infrared Absorption Spectrum (KBr) $\nu_{max}$ cm$^{-1}$: 1615, 1585, 1511, 1459, 1418.

Nuclear Magnetic Resonance Spectrum (CDCl$_3$) δ ppm: 2.73 (1H, AB-doublet of doublets, J=4.5 & 3.0 Hz); 2.87 (1H, AB-doublet of doublets, J=4.5 & 4.5 Hz); 3.26–3.50 (1H, multiplet); 4.20 (1H, AB-doublet of doublets, J=12.0 & 6.0 Hz); 4.58 (1H, AB-doublet of doublets, J=12.0 & 3.0 Hz); 6.20 (1H, singlet); 7.30–7.90 (5H, multiplet).

Further examples of preferred compounds of the formula I(a) of this invention include the following compounds:

Compound 1a

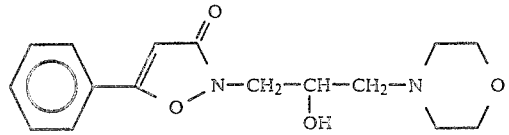

2-(2-hydroxy-3-morpholinopropyl)-5-phenyl-4-isoxazolin-3-one

Compound 2a

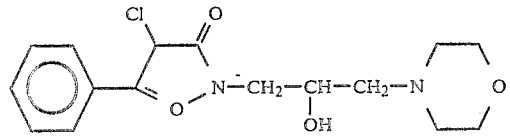

4-chloro-2-(2-hydroxy-3-morpholinopropyl)-5-phenyl-4-isoxazolin-3-one

Compound 3a

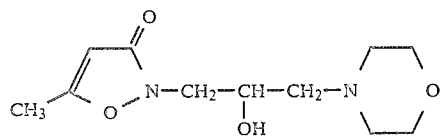

2-(2-hydroxy-3-morpholinopropyl)-5-methyl-4-isoxazolin-3-one

Compound 4a

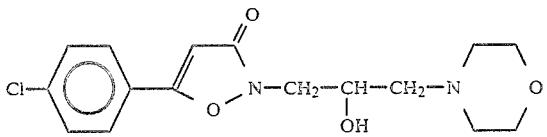

5-p-chlorophenyl-2-(2-hydroxy-3-morpholinopropyl)-4-isoxazolin-3-one

Compound 5a

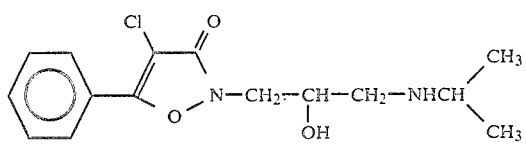

4-chloro-2-(2-hydroxy-3-isopropylaminopropyl)-5-phenyl-4-isoxazolin-3-one

Compound 6a

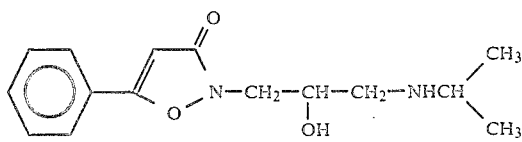

2-(2-hydroxy-3-isopropylaminopropyl)-5-phenyl-4-isoxazolin-3-one

Compound 7a

-continued

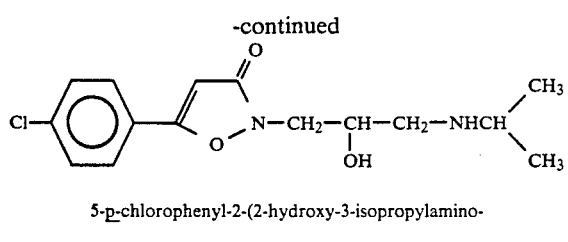

5-p-chlorophenyl-2-(2-hydroxy-3-isopropylamino-propyl)-4-isoxazolin-3-one

In addition, for use as a cerebral active drug, the following compounds are among the preferred:

Compound 8

2-(2-hydroxy-3-morpholinopropyl)-2,3-dihydro-1,2-benzoisoxazol-3-one;

Compound 9

2-(2-hydroxy-3-morpholinopropyl)-2,3,4,5,6,7-hexahydro-1,2-benzoisoxazol-3-one;

Furthermore, when used as a centrally-acting muscle relaxant and when $R^3$ and $R^4$ are an alicyclic amino group, the alicyclic amino group can be substituted by $C_1$–$C_4$ alkyl, $C_1$–$C_4$ alkoxy, hydroxy, halogen, nitro or trifluoromethyl groups.

The most preferred of these are compound 1a–3a.

In the present invention, the isoxazolin-3-one derivatives of formula (Ia) can be employed as pharmaceutically acceptable acid additional salts. The salts can be exemplified by inorganic acid salts such as a hydrochloride, hydrobromide or sulfate salt; and organic acid salts such as an oxalate, lactate, citrate, tartarate, succinate, maleate, fumarate or methanesulfonate salt. The hydrochloride is generally the most preferred.

Asymmetric carbon atoms exist in the compounds represented by the general formula (Ia), and the present invention embraces the use of optical isomers and any mixtures thereof.

Isoxazolin-3-one derivatives having the general formula (Ia) can be prepared according to known procedures such as the procedures described in the Japanese Patent, Laid-Open (Kokai), 56-34674.

Specifically, a 2-(3-halo-2-hydroxypropyl-4-isoxazolin-3-one can be reacted with an amine of formula $NHR^3R^4$, in accordance with the following reaction scheme:

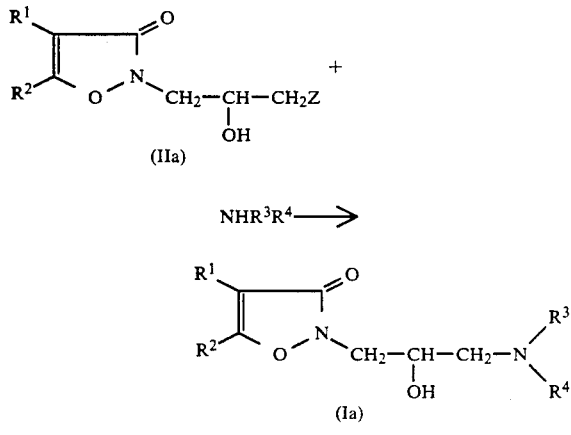

(where $R^1$, $R^2$, $R^3$ and $R^4$ are as defined, and Z represents a halogen atom for example chlorine, bromine or iodine).

For example, the isoxazoline-3-one of formula (IIa) can be reacted with the amine $NHR^3R^4$ in a solvent at reflux for several hours, and the product then isolated using conventional techniques. Further details can be found in the Japanese Kokai 56-34674.

EXPERIMENT 1

Suppression of decerebrate rigidity in rats

The suppression of decerebrate rigidity in laboratory animals, such as rats, is a well known model for control of human spasticity and/or rigidity.

In the test method, a rat was anesthetized with halothane and fixed on a stereotaxic apparatus (SR-5, Narishige). In accordance with the brain atlas by Pellegrino et al., [L. J. Pellegrino, A. S. Pellegrino & A. J. Cushman: A Stereotaxic Atlas of the Rat Brain, Plenum Press, New York and London (1967)], an electrode 0.7 mm in diameter, which was insulated except for 1 mm at the tip, was inserted bilaterally into the midbrain reticular formation (AP: 0, L: ±1.5, H: −3.0). A clip serving as the reference electrode was fixed on the temporal muscle. Through these electrodes, a high frequency electric current (100 KHz, 10 to 20 mA) was applied from a lesion generator (Glass Co., LM4A) for 2 to 3 minutes to cauterize electrically this brain region.

The rat was then immediately set free from the stereotaxic apparatus. A polyethylene cannula was inserted into the duodenum and fixed with an acrylic resin (Aron Alfa, Sankyo Co., Ltd.). After completion of these operations, halothane anesthesia was immediately discontinued.

After 1.5 hours, when the animal awoke from the anesthesia, the rat was fixed on an apparatus devised in our laboratory for a hind leg fixation. Both hind legs were fixed at the anterior part of the ankle joints. Both hindlimb paws were then pushed in 4 mm for 6 seconds in every minute. The resulting repulsive tension was drawn on a polygraph through a strain gauge.

The test compounds were suspended in a 0.5% w/v CMC (carboxymethyl cellulose) aqueous solution and were administered orally (p.o.) or intraperitoneally (i.p.).

The results are summarized in the following Table 7, where the compounds of the present invention are identified by the number of the foregoing Example in which each was prepared, Compound X is the known compound eperisone hydrochloride, and Compound Y is the known compound afloqualone.

TABLE 7

| | Inhibition of decerebrate rigidity in rats | | |
|---|---|---|---|
| Cpd. of Ex. No. | Dose (mg/kg) (Administration route) | Onset of the effect (minutes) | Maximum inhibition (%) | Duration of the effect (minutes) |
| 2 | 100 (i.p.) | 5 | 60 | >90 |
| 3 | 20 (p.o.) | 5 | 60 | >90 |
| 3 | 30 (p.o.) | 5 | 90 | >90 |
| 3 | 100 (p.o.) | 5 | 90 | >90 |
| 5 | 100 (p.o.) | 5 | 70 | >90 |
| 15 | 50 (i.p.) | 5 | 50 | >60 |
| 1a | 10 (i.d.) | 10 | 20 | >90 |
| 1a | 30 (i.d.) | 5 | 60 | >180 |
| 1a | 30 (p.o.) | 10 | 95 | >160 |
| 1a | 30 (i.p.) | 5 | 60 | >120 |
| 2a | 50 (i.p.) | 10 | 50 | >120 |
| 2a | 30 (p.o.) | 5 | 55 | >90 |

TABLE 7-continued

| | | Inhibition of decerebrate rigidity in rats | | |
|---|---|---|---|---|
| Cpd. of Ex. No. | Dose (mg/kg) (Administration route) | Onset of the effect (minutes) | Maximum inhibition (%) | Duration of the effect (minutes) |
| 2a | 50 (p.o.) | 5 | 90 | >90 |
| 2a | 100 (p.o.) | 5 | 100 | >90 |
| 3a | 50 (i.p.) | 5 | 30 | 50 |
| 4a | 50 (i.p.) | 5 | 80 | >120 |
| 5a | 50 (i.p.) | 5 | 95 | >120 |
| 6a | 50 (i.p.) | 5 | 30 | 60 |
| 7a | 50 (i.p.) | 5 | 75 | 60 |
| X | 10 (p.o.) | 10 | 30 | >30 |
| X | 30 (p.o.) | 10 | 30 | 45 |
| X | 50 (p.o.) | 10 | 50 | 30 |
| X | 100 (p.o.) | 5 | 50 | 60 |
| Y | 5 (p.o.) | 10 | 25 | 60 |
| Y | 10 (p.o.) | 10 | 55 | 45 |
| Y | 30 (p.o.) | 10 | 70 | 120 |

All of the compounds of the present invention were effective in suppressing decerebrate rigidity in rats, which is recognized as a model for spasticity and/or rigidity in humans, showing an activity comparable with, or better than, that of eperisone hydrochloride (Compound X) or afloqualone (Compound Y), both of which have already been used clinically as therapeutic agents for myotonia caused by cerebrovascular disorder sequelae.

EXPERIMENT 2

Suppression of decerebrate rigidity (cats)

Adult cats each weight 3.0 to 4.5 kg were used. Under ether anesthesia, the trachea was cannulated and the common carotid arteries were ligated at both sides. The cat was decerebrated by suction at the precollicular level. Ether anesthesia was then immediately discontinued. A pair of needle electrodes was inserted into the neck muscle in order to pick up any EMG muscular discharges. The EMG discharge was amplified and recorded on a pen-writing recorder, along with an integration of the EMG discharge. Recording was started at least 2 hours after withdrawal of anesthesia. Blood pressure induced from the femoral artery, as well as body temperature and heart beat, were recorded and monitored throughout the experiment.

After stable EMG discharges were obtained, the test compounds suspended in 0.5% CMC solution were administered into the duodenum through a previously inserted cannula. The effect of the test compound was expressed as the ratio of the integrated EMG discharge after administration relative to the value before administration.

At a dose of 100 mg/kg, both the Compounds 1a and 2a began to depress the decerebrate rigidity within 2 to 3 minutes of intraduodenal administration. About 30% and about 65% inhibitions were observed 5 minutes and 1 hour after administration, respectively. These inhibitory effects lasted throughout the observation period of 2 hours. On the other hand, similar administration of 50 mg/kg of eperisone hydrochloride (Compound 8), the control drug, induced vomiting immediately after administration accompanied with abrupt changes in blood pressure and heart beat. Although decerebrate rigidity was inhibited by eperisone hydrochloride, it returned 30 minutes after administration. This short duration was also observed in Experiment 1.

Thus, Compounds 1a and 2a reduced the decerebrate rigidity in cats, which is a model of myotonia as cerebral apoplectic sequelae. Both compounds were weaker in side effects and of longer action than eperisone hydrochloride, which is clinically used at present as a therapeutic agent for such a kind of condition.

EXPERIMENT 3

Effect on spinal reflex in cats

Adult cats weighing 3.0 to 4.5 kg each were used. After induction of anesthesia with ether, the animal was anesthetized by intravenous injection of 50 mg/kg of a-chloralose. After the trachea was cannulated, the animal was fixed on a stereotaxic apparatus, and the lumbosacral spinal cord was exposed by laminectomy from $L_3$ to $S_1$. The ventral roots of the right side were cut from $L_6$ to $S_1$ as distal as possible and the cut ends were ligated with cotton thread previously immersed in Ringer's solution. The exposed spinal cord was covered with warmed mineral oil and maintained at 37° C. The ventral root, either $L_7$ or $S_1$, was fixed on a pair of platinum wire electrodes. A pair of collar-type electrodes was implanted on the ipsilateral tibial nerve and the saphenous nerve, for stimulation. After completion of all these operations, the cat was immobilized with pancronium bromide (0.5 mg/kg, i.v.) and maintained by artificial respiration (40/minute). Recording was started at least 2 hours after withdrawal of ether anesthesia. A single square pulse (0.01 to 0.1 msecond pulse width, supramaximal intensity) was applied to the nerve at a frequency of 0.3 Hz from an electronic stimulator. The spinal monosynaptic reflex, polysynaptic reflex, and spino-bulbo-spinal reflex recorded from the ventral root were amplified, displayed on an oscilloscope, and the signals were averaged over ten signals using a signal processor. In a similar manner to Experiment 2, the blood pressure, heart beat and body temperature of the animal were recorded and monitored. Compounds to be tested were also administered in a similar manner.

After administration of a dose of 100 mg/kg of Compound 1a or Compound 2a, both the polysynaptic reflex and the spino-bulbo-spinal reflexes were remarkably inhibited, though the monosynaptic reflex was little affected. The onset of this effect was observed 5 minutes after administration, reaching its maximum after 30 minutes and continuing for about 2 hours. A similar effect was observed by similar administration of 100 mg/kg of chlorphenesin carbamate. Therefore, Compounds 1a and 2a were shown to be interneuron blockers, like chlorphenesin carbamate.

EXPERIMENT 4

Potentiation of thiopental anesthesia (mice)

In the test method, male adult mice of ddY strain each weighing 20 to 30 g were used as divided groups each made up of 5 to 7 mice. Test compounds suspended in 0.5% CMC solution were orally administered. After one hour, thiopental (30 mg/kg) was injected into the tail vein, and the time required for the mouse to recover the righting reflex was measured.

The results are summarized in the following table.

TABLE 8

| Effect on duration of thiopental anesthesia | | | |
|---|---|---|---|
| Compound | Dose (mg/kg) | Animal number | Anesthesia time (sec.) |
| 1a | 0 | 7 | 254.7 ± 19.5 |
| 1a | 50 | 8 | 288.5 ± 20.1 |
| 1a | 100 | 7 | 237.3 ± 25.5 |

TABLE 8-continued

| Effect on duration of thiopental anesthesia | | | |
|---|---|---|---|
| Compound | Dose (mg/kg) | Animal number | Anesthesia time (sec.) |
| 2a | 0 | 10 | 275.3 ± 18.6 |
| 2a | 100 | 9 | 329.1 ± 81.2 |
| X | 0 | 10 | 206.0 ± 13.1 |
| X | 10 | 5 | 182.0 ± 9.8 |
| X | 30 | 5 | 192.0 ± 18.3 |
| X | 100 | 5 | 247.0 ± 34.9 |
| Y | 0 | 10 | 206.0 ± 13.1 |
| Y | 10 | 5 | 242.0 ± 10.0 |
| Y | 30 | 5 | 4657.0 ± 636.6* |

*= $P < 0.001$

Compounds 1a and 2a did not significantly prolong the duration of thiopental-induced anesthesia in comparison with eperisone hydrochloride (Compound X), which has already been used clinically as a centrally-acting muscle relaxant. On the other hand, afloqualone (Compound Y) which has also been used for this purpose, did significantly prolong the duration of anesthesia at an effective dose of 30 mg/kg. This fact implies that Compounds 1a and 2a induce drowsiness (the adverse effect) less than afloqualone.

EXPERIMENT 5

Improvement of ischemia-induced neurological symptoms in the Mongolian Gerbil caused by ligation of the bilateral common carotid arteries for 30 minutes The test animals employed were male adult Mongolian gerbils (16-20 weeks old). These were used in groups each consisting of from 10 to 20 animals. The bilateral common carotid arteries were occluded for 30 minutes under anesthesia with pentobarbital (30 mg/kg, intraperitoneally) and halothane (it was introduced to a mixture of 95% oxygen and 5% carbon dioxide at a concentration of 1.5% by volume) and then the occlusion was released to allow the blood to flow. The animal was then placed in a supine position, and we measured (1) the time taken from recommencement of blood flow until convulsions occurred and (2) the survival time. Observations to determine the onset time of convulsions and the survival time were continued for 6 and 7 hours, respectively, after recommencement of blood flow. If no convulsions occurred within 6 hours after the recommencement of blood flow, the onset time of convulsions was assumed to be 360 minutes, and, if the animal did not die within 7 hours, the survival time was recorded as 420 minutes for calculation purposes. The compound to be tested was suspended in a 0.5% w/v carboxymethyl cellulose (CMC) aqueous solution and administered intraperitoneally upon recommencement of blood flow in the common carotid arteries. The dose of test compound administered was 100 mg/kg, and the compound used is as shown in the following Table 9. On the other hand, a 0.5% CMC solution containing no test compound was administered likewise to a control group. Statistical analysis was carried out using the Mann-Whitney U-test between the control group and the test group.

The results are shown in Table 9. As can be seen from these results, in the group to which the compounds of the present invention were administered at a dose of 100 mg/kg, both onset time of convulsions and survival time were significantly prolonged.

TABLE 9

| Cpd. of Ex. No. | No. of animals | Dose (mg/kg) | Recovery time of righting reflex (min.) | Onset time of convulsions (min.) | Survival time (min.) |
|---|---|---|---|---|---|
| Control | 18 | 0 | 107.7 ± 10.0 | 183.5 ± 17.4 | 282.3 ± 13.9 |
| 4 | 18 | 100 | 115.7 ± 8.7 | 233.9 ± 12.2* | 344.2 ± 15.1*** |
| Control | 17 | 0 | — | 198.8 ± 19.9 | 300.6 ± 14.3 |
| Compound 2a hydrochloride | 17 | 100 | — | 289.4 ± 11.9 | 375.7 ± 10.5 |

*= $p < 0.05$.
***= $p < 0.01$.

EXPERIMENT 6

Improvement in ischemia-induced neurological symptoms in Spontaneously Hypertensive Rats Stroke Prone (SHR SP) caused by ligation of the bilateral common arotid arteries The test animals employed were male adult SHR SPs (13 or 15 weeks old). They were used in groups each consisting of about 10 animals. Under halothane anesthesia, both common carotid arteries of each animal were ligated to prepare a brain ischemia model. The halothane anesthesia was stopped immediately after the ligation, and then the time taken to recover the righting reflex, the onset time of convulsions and the survival time were determined. The test solution was prepared in the same manner as described in Experiment 1 and was administered to the animal intraperitoneally 30 minutes before the ligation. A 0.5% CMC solution was administered to the control group in the same manner. The statistical analysis was carried out in a similar manner to that in Experiment 1. The statistical analysis of the survival rate was carried out by the $X^2$ test.

The results are shown in Table 10. As can be seen in Table 10, these compounds prolonged onset time of convulsions, survival time significantly at doses of 100 mg/kg (compounds 2a, 3, 4, 20) and 30 mg/kg (compounds 3 and 20).

Further compound 3 increased survival rate of ischemic animals at a dose of 100 mg/kg.

TABLE 10

| Cpd of Ex. No. | Dose (mg/kg) | No. & (age) of animals | Recovery time of righting reflex (min.) | Onset time of convulsions (min.) | Survival time (min.) | Survival rate (%) |
|---|---|---|---|---|---|---|
| Cont | 0 | 10 (13) | 9.9 ± 2.7 | 97.5 ± 20.7 | 200.6 ± 35.2 | 0.0 |
| 4 | 100 | 9 (13) | 10.1 ± 1.8 | 97.6 ± 18.0 | 322.4 ± 34.8** | 44.4 |
| Cont | 0 | 10 (13) | 9.1 ± 3.2 | 59.7 ± 7.0 | 273.5 ± 45.0 | 40.0 |
| 3 | 30 | 10 (13) | 7.1 ± 0.9 | 106.5 ± 9.9*** | 392.2 ± 21.2 | 80.0 |
| 3 | 100 | 10 (13) | 36.3 ± 16.7* | 306.9 ± 17.1*** | 420.0 ± 0.0* | 100** |
| Cont | 0 | 11 (15) | 8.7 ± 1.8 | 48.3 ± 6.6 | 225.6 ± 34.2 | 18.2 |
| 20 | 30 | 11 (15) | 6.5 ± 0.6 | 71.9 ± 9.3* | 295.9 ± 32.3 | 36.4 |
| 20 | 100 | 11 (15) | 6.9 ± 0.9 | 176.7 ± 25.8** | 371.9 ± 26.3*** | 63.6# |
| Cont | 0 | 11 (15) | 15.5 ± 2.1 | 50.5 ± 6.5 | 226.7 ± 26.7 | — |

TABLE 10-continued

| Cpd of Ex. No. | Dose (mg/kg) | No. & (age) of animals | Recovery time of righting reflex (min.) | Onset time of convulsions (min.) | Survival time (min.) | Survival rate (%) |
|---|---|---|---|---|---|---|
| Compound 2a | 30 | 11 (15) | 8.0 ± 1.7 | 99.8 ± 27.8 | 232.1 ± 35.8 | — |
| hydro-chloride | 100 | 11 (15) | 7.6 ± 1.7 | 103.5 ± 16.2 | 233.0 ± 28.7 | — |

$^{\#}$ = p < 0.10.
$^{\circ}$ = p < 0.05.
$^{\circ\circ}$ = p < 0.02.
$^{\circ\circ\circ}$ = p < 0.01.
— = Survival rate not determined

EXPERIMENT 7

Effect on survival time under hypoxic conditions

The test animals employed were male adult mice (5 weeks old and about 30 g body weight) of the ddY strain. The animals were employed in groups, each containing from 7 to 17 animals. Each animal was given intraperitoneally a test compound in suspension (as in the preceding Experiments). Thirty (30) minutes after this administration, 2 or 3 animals were placed in a 1.5 liter gas chamber made of acrylate resin, and a mixture of 4% by volume oxygen and 96% nitrogen was supplied at the rate of 10 liters/minute. The time of death of the animal was measured (determined by the cessation of respiration).

The results are shown in the following Table 11.

TABLE 11

| Cpd. of Ex. No. | Dose (mg/kg) | No. of test animals | Survival time (seconds) |
|---|---|---|---|
| Cont. | 0 | 11 | 115.5 ± 8.3 |
| 3 | 30 | 7 | 213.0 ± 27.5** |
| 3 | 100 | 7 | 446.7 ± 36.9**** |
| Cont. | 0 | 17 | 92.2 ± 5.3 |
| 20 | 30 | 14 | 124.6 ± 15.4*** |
| 20 | 100 | 9 | 349.5 ± 59.1*** |
| Cont. | 0 | 12 | 144.9 ± 10.8 |
| 4 | 100 | 12 | 178.9 ± 15.0*** |

** = p < 0.02.
*** = p < 0.01.
**** = p < 0.001.

As can be seen from the above results, the compounds of the present invention were found to improve significantly the survival time of the test animals under hypoxic conditions.

EXPERIMENT 8

Acute toxicity

Each of the test compounds used in the above Experiments 1 to 7 was suspended in a 0.5% w/v CMC aqueous solution, and 1000 mg/kg of the compound was orally administered to each of 3 male adult mice of the ddY strain (weighing 20 to 25 g each) which were then observed for 5 days. In some cases, systemic hypotonia attributed to the effect of the drug was observed for about 3 hours after administration, but all of the mice survived.

We claim:

1. A compound which is represented by the formula (Ic):

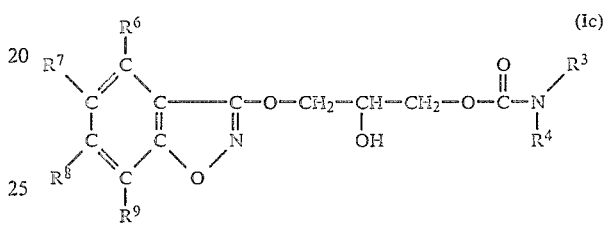

in which:

$R^3$ and $R^4$ are independently selected from the group consisting of hydrogen atoms, $C_1$–$C_4$ alkyl groups, benzyl groups, benzyl groups having at least one substituent selected from the group consisting of substituents (a), phenyl groups and phenyl groups having at least one substituent selected from the group consisting of substituents (a); or $R^3$, $R^4$ and nitrogen atom to which they are attached together represent an alicyclic amino group having a total of 5 or 6 ring atoms, of which one is said nitrogen atom and 0 or 1 is an additional hetero-atom selected from the group consisting of nitrogen, oxygen and sulfur hetero-atoms, said alicyclic amino group being unsubstituted or, where there is an additional nitrogen hetero-atom, having at least one substituent on that additional nitrogen hetero-atom selected from the group consisting of substituents (b), defined below; and one of $R^6$, $R^7$, $R^8$ and $R^9$ represents a hydrogen atom, a halogen atom, a $C_1$–$C_4$ alkyl group or a $C_1$–$C_4$ alkoxy group, and the others all represent hydrogen atoms; wherein substituents (a) are defined as follows:
$C_1$–$C_4$ alkyl groups, $C_1$–$C_4$ alkoxy groups, hydroxy groups, halogen atoms, nitro groups, amino groups, trifluoro amino and $C_2$–$C_4$ aliphatic carboxylic acylamino groups;

substituents (b) are defined as follows:
$C_1$–$C_3$ alkyl groups, $C_1$–$C_3$ alkoxy groups, hydroxy groups, halogen atoms, nitro groups, amino groups, $C_2$–$C_4$ aliphatic carboxylic acylamino groups, benzyl groups, benzyl groups having at least one substituent selected from the group consisting of substituents (a), defined above, phenyl groups and phenyl groups having at least one substituent selected from the group consisting of substituents (a) defined above;

or a pharmaceutically acceptable salt thereof.

2. A compound which is represented by the formula (Ie):

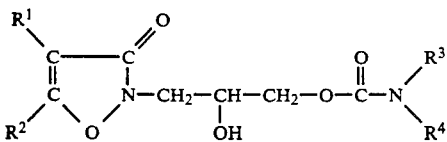

(Ie)

in which:
- $R^1$ represents a hydrogen atom, a halogen atom, a $C_1$–$C_4$ alkyl group, a $C_2$–$C_4$ alkenyl group, a $C_2$–$C_4$ alkynyl group, a benzyl group, a benzyl group having at least one substituent selected from the group consisting of substituents (a), a phenyl group or a phenyl group having at least one substituent selected from the group consisting of substituents (a);
- $R^2$ represents a hydrogen atom, a $C_1$–$C_4$ alkyl group, a phenyl group, a phenyl group having at least one substituent selected from the group consisting of substituents (a), or a heterocyclic group having 5 or 6 ring atoms, of which from 1 to 3 are heteroatoms selected from the group consisting of nitrogen, oxygen and sulfur hetero-atoms, said heterocyclic group being unsubstituted or having at least one substituent selected from the group consisting of substituents (a), defined below;
- $R^1$ and $R^2$, together with the carbon atoms to which they are attached, represent a hydrocarbon ring fused to the isoxazole ring and having, in total, from 5 to 7 ring carbon atoms, said hydrocarbon ring being unsubstituted or having at least one substituent selected from the group consisting of substituents (b), defined below;
- $R^3$ and $R^4$ are independently selected from the group consisting of hydrogen atoms, $C_1$–$C_4$ alkyl groups, benzyl groups, benzyl groups having at least one substituent selected from the group consisting of substituents (a), phenyl groups and phenyl groups having at least one substituent selected from the group consisting of substituents (a);
- $R^3$, $R^4$ and the nitrogen atom to which they are attached together represent an alicyclic amino group having a total of 5 or 6 ring atoms, of which one is said nitrogen atom and 0 or 1 is an additional hetero-atom selected from the group consisting of nitrogen, oxygen and sulfur hetero-atoms; said alicyclic amino group being unsubstituted or, where there is an additional nitrogen hetero-atom, having at least one substituent on that additional nitrogen hetero-atom selected from the group consisting of substituents (b), defined below;

wherein
substituents (a) are as defined below:
$C_1$–$C_4$ alkyl groups, $C_1$–$C_4$ alkoxy groups, hydroxy groups, halogen atoms, nitro groups, amino groups, trifluoro amino and $C_2$–$C_4$ aliphatic carboxylic acylamino groups; and
substituents (b) are as defined below
$C_1$–$C_3$ alkyl groups, $C_1$–$C_3$ alkoxy groups, hydroxy groups, halogen atoms, nitro groups, amino groups, $C_2$–$C_4$ aliphatic carboxylic acylamino groups, benzyl groups, benzyl groups having at least one substituent selected from the group consisting of substituents (a), defined above, phenyl groups and phenyl groups having at least one substituent selected from the group consisting of substituents (a), defined above;

or a pharmaceutically acceptable salt thereof.

3. A compound represented by the formula (If):

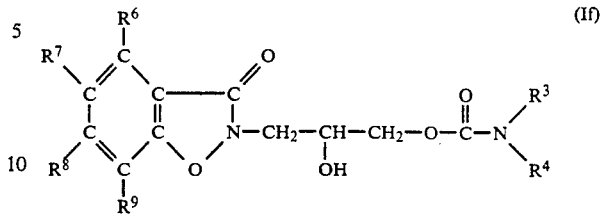

(If)

in which:
- $R^3$ and $R^4$ are independently selected from the group consisting of hydrogen atoms, $C_1$–$C_4$ alkyl groups, benzyl groups, benzyl groups having at least one substituent selected from the group consisting of substituents (a), phenyl groups and phenyl groups having at least one substituent selected from the group consisting of substituents (a); or
- $R^3$, $R^4$ and the nitrogen atom to which they are attached together represent an alicyclic amino group as defined in claim 1; and
- one of $R^6$, $R^7$, $R^8$ and $R^9$ represents a hydrogen atom, a halogen atom, a $C_1$–$C_4$ alkyl group or a $C_1$–$C_4$ alkoxy group, and the others all represent hydrogen atoms;

wherein substituents (a) are defined as follows:
$C_1$–$C_4$ alkyl groups, $C_1$–$C_4$ alkoxy groups, hydroxy groups, halogen atoms, nitro groups, amino groups, trifluoro amino and $C_2$–$C_4$ aliphatic carboxylic acylamino groups;

or a pharmaceutically acceptable salt thereof.

4. A compound which is represented by the formula (Ib):

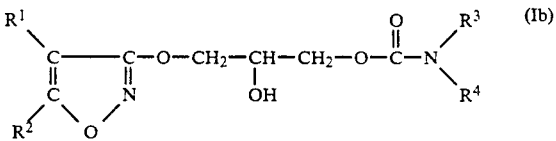

(Ib)

in which:
- $R^1$ represents a hydrogen atom, a halogen atom or a $C_1$–$C_4$ alkyl group;
- $R^2$ represents a phenyl group or a phenyl group having at least one substituent selected from the group consisting of substituents (c), defined below;
- substituents (c):
  $C_1$–$C_3$ alkoxy groups, hydroxy groups and halogen atoms;
- $R^1$ and $R^2$, together with the carbon atoms to which they are attached, represent a 6-membered hydrocarbon ring fused to the isoxazole ring and being unsubstituted or having at least one substituent selected from the group consisting of halogen atoms; and
- $R^3$ and $R^4$ are independently selected from the group consisting of hydrogen atoms, $C_1$–$C_4$ alkyl groups, benzyl groups and phenyl groups; or
- $R^3$, $R^4$ and the nitrogen atom to which they are attached together represent an alicyclic amino group having a total of 5 or 6 ring atoms, of which one is said nitrogen atom and 0 or 1 is an additional nitrogen hetero-atom, said alicyclic amino group being unsubstituted or, where there is an additional nitrogen hetero-atom, having at least one substituent on that additional nitrogen hetero-atom selected from the group consisting of substituents (d), defined below;

substituents (d):
C$_1$–C$_3$ alkyl groups, benzyl groups and phenyl groups.

5. A compound which is represented by the formula (Ib):

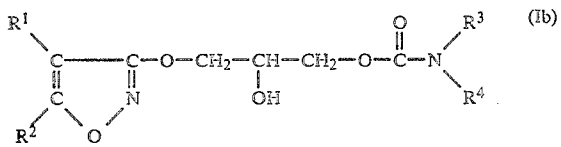

in which:
R$^1$ represents a hydrogen atom, a chlorine atom or a C$_1$ or C$_2$ alkyl group;
R$^2$ represents a phenyl group or a phenyl group having at least one substituent selected from the group consisting of substituents (c'), defined below; or
R$^1$ and R$^2$, together with the carbon atoms to which they are attached, represent a benzene ring fused to the isoxazole ring and being unsubstituted or having one substituent selected from the group consisting of halogen atoms; and substituents (c'):
methoxy groups and halogen atoms;

R$^3$ and R$^4$ are independently selected from the group consisting of hydrogen atoms, methyl groups and ethyl groups; or R$^3$, R$^4$ and the nitrogen atom to which they are attached together represent a morpholino group, a 1-piperazinyl group, a 4-methyl-1-piperazinyl group, a 1-pyrrolidinyl group or a piperidino group.

6. A compound, selected from the group consisting of:
3-(3-carbamoyloxy-2-hydroxypropoxy)-5-(m-chlorophenyl)isoxazole;
and pharmaceutically acceptable salts thereof.

7. A compound, selected from the group consisting of:
3-(2-hydroxy-3-morpholinopropoxy)-5-phenylisoxazole;
and pharmaceutically acceptable salts thereof.

8. A compound, selected from the group consisting of:
3-(2-hydroxy-3-morpholinopropoxy)-4-methyl-5-phenylisoxazole;
and pharmaceutically acceptable salts thereof.

9. A compound, selected from the group consisting of:
3-(3-carbamoyloxy-2-hydroxypropoxy)-5-chloro-1,2-benzisoxazole;
and pharmaceutically acceptable salts thereof.

10. A method of treating a cerebrovascular disorder by the administration to a mammal suffering from or prone to cerebrovascular disorders of an effective amount of at least one cerebro-active drug, wherein said cerebro-active drug is represented by the formula (Ib):

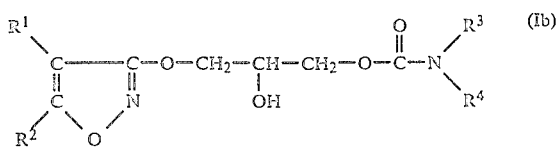

in which:
R$^1$ represents a hydrogen atom, a halogen atom or a C$_1$–C$_4$ alkyl group;
R$^2$ represents a phenyl group or a phenyl group having at least one substituent selected from the group consisting of substituents (c), defined below;

substituents (c):
C$_1$–C$_3$ alkoxy groups, hydroxy groups and halogen atoms; or R$^1$ and R$^2$, together with the carbon atoms to which they are attached, represent a 6-membered hydrocarbon ring fused to the isoxazole ring and being unsubstituted or having at least one substituent selected from the group consisting of halogen atoms; and R$^3$ and R$^4$ are independently selected from the group consisting of hydrogen atoms, C$_1$–C$_4$ alkyl groups, benzyl groups and phenyl groups, or R$^3$, R$^4$ and the nitrogen atom to which they are attached together represent an alicyclic amino group having a total of 5 or 6 ring atoms, of which one is said nitrogen atom and 0 or 1 is an additional nitrogen hetero-atom, said alicyclic amino group being unsubstituted or, where there is an additional nitrogen hetero-atom, having at least one substituent on that additional nitrogen hetero-atom selected from the group consisting of substituents (d), defined below;

substituents (d):
C$_1$–C$_3$ alkyl groups, benzyl groups and phenyl groups.

11. A method of treating a cerebrovascular disorder by the administration to a mammal suffering from or prone to cerebrovascular disorders an effective amount of at least one cerebro-active drug, wherein said cerebro-active drug is represented by the formula (Ib):

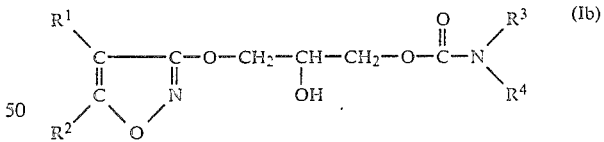

in which:
R$^1$ represents a hydrogen atom, a chlorine atom or a C$_1$ or C$_2$ alkyl group;
R$^2$ represents a phenyl group or a phenyl group having at least one substituent selected from the group consisting of substituents (c'), defined below; or
R$^1$ and R$^2$, together with the carbon atoms to which they are attached, represent a benzene ring fused to the isoxazole ring and being unsubstituted or having one substituent selected from the group consisting of halogen atoms; and substituents (c'):
methoxy groups and halogen atoms;

R$^3$ and R$^4$ are independently selected from the group consisting of hydrogen atoms, methyl groups and ethyl groups;

$R^3$, $R^4$ and the nitrogen atom to which they are attached together represent a morpholino group, a 1-piperazinyl group, a 4-methyl-1-piperazinyl group, a 1-pyrrolidinyl group or a piperidino group.

12. A method of effecting centrally-acting muscle relaxant activity, which comprises administering an effective amount of an active compound to a mammal wherein the active compound is a compound of formula (I)

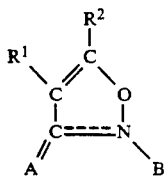

in which: either
 (a) the dotted line (==) represents a single bond;
  A= represents a oxygen atom; and
  B represents a group of formula (II):

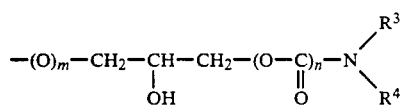

in which m is 0 and n is 0 or 1; or
 (b) the dotted line (==) represents a double bond;
  A= represents said group of formula (II) in which m is 1 and n is 0 or 1; and
  B is absent; and
R' represents a hydrogen atom, a halogen atom, a $C_1$-$C_4$ alkyl group, a $C_2$-$C_4$ alkenyl group, a $C_2$-$C_4$ alkynyl group, a benzyl group, a benzyl group having at least one substituent selected from the group consisting of substituents (a), defined below, a phenyl group or a phenyl group having at least one substituent selected from the group consisting of substituents (a), defined below;
$R^2$ represents a hydrogen atom, a halogen atom, a $C_1$-$C_4$ alkyl group, a phenyl group, a phenyl group having at least one substituent selected from the group consisting of substituents (a), defined below, or a heterocyclic group having 5 or 6 ring atoms, of which from 1 to 3 are hetero-atoms selected from the group consisting of nitrogen, oxygen and sulfur hetero-atoms, said heterocyclic group being unsubstituted or having at least one substituent selected from the group consisting of substituents (a), defined below; or
$R^1$ and $R^2$, together with the carbon atoms to which they are attached, represent a hydrocarbon ring fused to the isoxazole ring and having, in total, from 5 to 7 ring carbon atoms, said hydrocarbon ring being unsubstituted or having at least one substituent selected from the group consisting of substituents (b), defined below;
$R^3$ and $R^4$ are independently selected from the group consisting of hydrogen atoms, $C_1$-$C_4$ alkyl groups, benzyl groups, benzyl groups having at least one substituent selected from the group consisting of substituents (a), defined below, phenyl groups and phenyl groups having at least one substituent selected from the group consisting of substituents (a), defined below; or $R^3$, $R^4$ and the nitrogen atom to which they are attached together represent an alicyclic amino group having a total of 5 or 6 ring atoms, of which one is said nitrogen atom and 0 or 1 is an additional hetero-atom selected from the group consisting of nitrogen, oxygen and sulfur hetero-atoms, said alicyclic amino group being unsubstituted or, where there is an additional nitrogen hetero-atom, having at least one substituent on that additional nitrogen hetero-atom selected from the group consisting of substituents (b), defined below;
substituents (a) can be:
 $C_1$-$C_4$ alkyl groups, $C_1$-$C_4$ alkoxy groups, hydroxy groups, halogen atoms, nitro groups, amino groups, trifluoro amino and $C_2$-$C_4$ aliphatic carboxylic acylamino groups; or:
 $C_1$-$C_3$ alkyl groups, $C_1$-$C_3$ alkoxy groups, hydroxy groups, halogen atoms, nitro groups, amino groups and $C_2$-$C_4$ aliphatic carboxylic acylamino groups; or:
 especially for compounds of the formula (I-0) wherein both m and n are 0:
 $C_1$-$C_4$ alkyl groups, $C_1$-$C_4$ alkoxy groups, hydroxy groups, halogen atoms, nitro groups, and trifluoro amino groups;
substituents (b):
 $C_1$-$C_3$ alkyl groups, $C_1$-$C_3$ alkoxy groups, hydroxy groups, halogen atoms, nitro groups, amino groups, $C_2$-$C_4$ aliphatic carboxylic acylamino groups, benzyl groups, benzyl groups having at least one substituent selected from the group consisting of substituents (a), defined above, phenyl groups and phenyl groups having at least one substituent selected from the group consisting of substituents (a), defined above; provided that:
 where A represents said group of formula (II) and n is 0, $R_1$ and $R_2$ together represent a benzene ring fused to the isoxazole ring and $R_4$ represents an alkyl group, then $R_3$ does not represent a hydrogen atom;
or a pharmaceutically acceptable salt thereof.

13. The method of claim 12, wherein said active compound is represented by the formula (Ib):

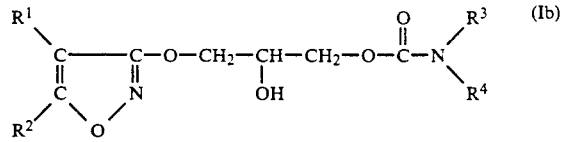

in which:
$R^1$ represents a hydrogen atom, a halogen atom or a $C_1$-$C_4$ alkyl group;
$R^2$ represents a phenyl group or a phenyl group having at least one substituent selected from the group consisting of substituents (c), defined below;
substituents (c):
 $C_1$-$C_3$ alkoxy groups, hydroxy groups and halogen atoms; or
$R^1$ and $R^2$, together with the carbon atoms to which they are attached, represent a 6-membered hydrocarbon ring fused to the isoxazole ring and being unsubstituted or having at least one substituent selected from the group consisting of halogen atoms; and R³ and R⁴ are independently selected from the group consisting of hydrogen atoms, $C_1$-$C_4$ alkyl groups, benzyl groups and phenyl groups. or R³, R⁴ and the nitrogen atom to which they are attached together represent an alicyclic amino group having a total of 5 or 6 ring atoms, of which one is said nitrogen atom and 0 or 1 is an additional nitrogen hetero-atom, said alicyclic amino group being unsubstituted or, where there is an additional nitrogen hetero-atom, having at least one substituent on that additional nitrogen hetero-atom selected from the group consisting of substituents (d), defined below;

substituents (d):

$C_1$-$C_3$ alkyl groups, benzyl groups and phenyl groups.

14. The method of claim 12, wherein said active compound is represented by the formula (Ib):

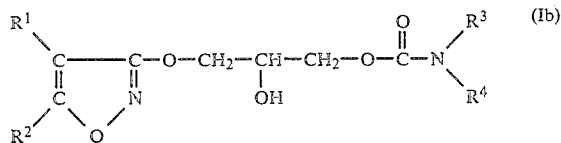

in which:

R¹ represents a hydrogen atom, a chlorine atom or a $C_1$ or $C_2$ alkyl group;

R² represents a phenyl group or a phenyl group having at least one substituent selected from the group consisting of substituents (c'), defined below; or R¹ and R², together with the carbon atoms to which they are attached, represent a benzene ring fused to the isoxazole ring and being unsubstituted or having one substituent selected from the group consisting of halogen atoms; and substituents (c'):

methoxy groups and halogen atoms;

R³ and R⁴ are independently selected from the group consisting of hydrogen atoms, methyl groups and ethyl groups; or R³, R⁴ and the nitrogen atom to which they are attached together represent a morpholino group, a 1-piperazinyl group, a 4-methyl-1-piperazinyl group, a 1-pyrrolidinyl group or a piperidino group.

15. The method of claim 12, wherein said active compound is selected from the group consisting of:

2-(2-hydroxy-3-morpholinopropyl)-4-methyl-5-phenyl-3-isoxazolone;

3-(3-carbamoyloxy-2-hydroxypropoxy)-5-(m-chlorophenyl)isoxazole;

3-(2-hydroxy-3-morpholinopropoxy)-5-phenylisoxazole;

3-(2-hydroxy-3-morpholinopropoxy)-4-methyl-5-phenylisoxazole;

3-(3-carbamoyloxy-2-hydroxypropoxy)-5-chloro-1,2-benzisoxazole;

and pharmaceutically acceptable salts thereof.

16. A pharmaceutical composition for the treatment of cerebrovascular disorders or as a centrally-acting muscle relaxant, which composition comprises an effective amount of an active compound, wherein said active compound is represented by the formula (Ib):

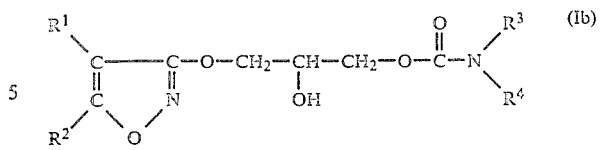

in which:

R¹ represents a hydrogen atom, a chlorine atom or a $C_1$ or $C_2$ alkyl group;

R² represents a phenyl group or a phenyl group having at least one substituent selected from the group consisting of substituents (c'), defined below;

R¹ and R², together with the carbon atoms to which they are attached, represent a benzene ring fused to the isoxazole ring and being unsubstituted or having one substituent selected from the group consisting of halogen atoms; and substituents (c'):

methoxy groups and halogen atoms;

R³ and R⁴ are independently selected from the group consisting of hydrogen atoms, methyl groups and ethyl groups; or R³, R⁴ and the nitrogen atom to which they are attached together represent a morpholino group, a 1-piperazinyl group, a 4-methyl-1-piperazinyl group, a 1-pyrrolidinyl group or a piperidino group.

17. A method of relaxing muscles in a mammal requiring such treatment which comprises administering to said mammal, an effective amount of a centrally-acting muscle relaxant, said muscle relaxant being a compound of the formula:

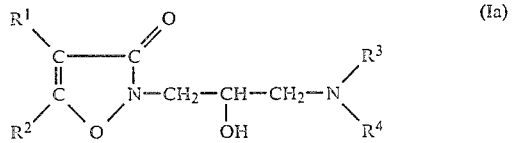

wherein:

R¹ is selected from the group consisting of hydrogen and halogen atoms;

R² is selected from the group consisting of alkyl groups with 1 to 4 carbon atoms, phenyl groups, phenyl groups substituted with 1 to 3 substituents, heterocyclic groups, and heterocyclic groups substituted with 1 to 3 substituents, said 1 to 3 substituents being selected from the group consisting of alkyl groups with 1 to 4 carbon atoms, alkoxy groups with 1 to 4 carbon atoms, hydroxy groups, halogen atoms, nitro groups, and trifluoromethyl, groups, and said heterocyclic groups having 5 or 6 ring atoms which include 1 to 3 heteroatoms selected from the group consisting of oxygen, sulphur, and nitrogen heteroatoms; or R¹ and R² together with the intervening carbon atoms form a 6- or 7-membered hydrocarbon ring;

R³ is selected from the group consisting of hydrogen atoms and alkyl groups having from 1 to 4 carbon atoms;

R⁴ represents an alkyl group having 1 to 4 carbon atoms; or

R³ and R⁴ together with the intervening nitrogen atom form a 5- or 6-membered alicyclic amino group optionally having at least one further heteroatom selected from the group consisting of oxygen, sulphur and nitrogen heteroatoms, said nitrogen heteroatom optionally being substituted with an alkyl group having 1 to 4 carbon atoms;

or a pharmaceutically acceptable salt thereof.

18. The method of claim 17, wherein, in said active compound, $R^1$ is as defined and $R^2$ is selected from the group consisting of alkyl groups with 1 to 4 carbon atoms, phenyl groups, and phenyl groups substituted with 1 to 3 substituents; or $R^1$ and $R^2$ together with the intervening carbon atoms form a benzene ring;

$R^3$ is a hydrogen atom and $R^4$ represents an alkyl group having 1 to 4 carbon atoms; or $R^3$ and $R^4$ together with the intervening nitrogen atom form an alicyclic amino group which is a 5-membered alicyclic amino group, or a 6-membered alicyclic amino group having at least one further heteroatom selected from the group consisting of oxygen heteroatoms, nitrogen heteroatoms and nitrogen heteroatoms substituted with an alkyl group having 1 to 4 carbon atoms.

19. The method of claim 17, wherein, in said active compound, $R^1$ is selected from the group consisting of hydrogen atoms, fluorine atoms, chlorine atoms, and bromine atoms;

$R^2$ is selected from the group consisting of alkyl groups with 1 to 4 carbon atoms, phenyl groups, and phenyl groups substituted with 1 to 3 substituents selected from fluorine atoms, chlorine atoms, bromine atoms, alkoxy group having from 1 to 4 carbon atoms, and hydroxy groups;

$R^3$ is a hydrogen atom and $R^4$ represents an alkyl group having 1 to 4 carbon atoms; or $R^3$ and $R^4$ together with the intervening nitrogen atom form a morpholino, 1-piperazinyl, 4-methyl-1-piperazinyl, or piperidino group.

20. The method of claim 17, wherein said active compound is selected from the group consisting of 2-(2-hydroxy-3-morpholinopropyl)-5-phenyl-4-isoxazolin-3-one;

4-chloro-2-(2-hydroxy-3-morpholinopropyl)-5-phenyl-4-isoxazolin-3-one;

2-(2-hydroxy-3-morpholinopropyl)-5-methyl-4-isoxazolin-3-one;

5-p-chlorophenyl-2-(2-hydroxy-3-morpholinopropyl)-4-isoxazolin-3-one;

4-chloro-2-(2-hydroxy-3-isopropylaminopropyl)-5-phenyl-4-isoxazolin-3-one;

2-(2-hydroxy-3-isopropylaminopropyl)-5-phenyl-4-isoxazolin-3-one;

5-p-chlorophenyl-2-(2-hydroxy-3-isopropylaminopropyl)-4-isoxazolin-3-one; and pharmaceutically acceptable salts of these compounds.

21. The method of claim 20, wherein said active compound is selected from the group consisting of:

2-(2-hydroxy-3-morpholinopropyl)-5-phenyl-4-isoxazolin-3-one;

4-chloro-2-(2-hydroxy-3-morpholinopropyl)-5-phenyl-4-isoxazolin-3-one; and pharmaceutically acceptable salts thereof.

22. The method of claim 17, wherein said active compound is administered by an administration mode selected from oral administration and parenteral administration.

23. The method of claim 22, wherein said active compound is administered as a composition selected from tablets, capsules, granules, powders, syrups, injections and suppositories.

24. The method of claim 22, wherein said active compound is administered at a dose of 5 mg to 50 mg given orally to adult humans, 1 to 3 times a day.

25. The method of claim 20, wherein said active compound is selected from the group consisting of:

4-chloro-2-(2-hydroxy-3-morpholinopropyl)-5-phenyl-4-isoxazolin-3-one; and pharmaceutically acceptable salts thereof.

26. The method of claim 20, wherein said active compound is selected from the group consisting of:

2-(2-hydroxy-3-morpholinopropyl)-5-methyl-4-isoxazolin-3-one; and pharmaceutically acceptable salts thereof.

27. The method of claim 20, wherein said active compound is selected from the group consisting of:

5-p-chlorophenyl-2-(2-hydroxy-3-morpholinopropyl)-4-isoxazolin-3-one; and pharmaceutically acceptable salts thereof.

28. The method of claim 20, wherein said active compound is selected from the group consisting of:

4-chloro-2-(2-hydroxy-3-isopropylaminopropyl)-5-phenyl-4-isoxazolin-3-one; and pharmaceutically acceptable salts thereof.

29. The method of claim 20, wherein said active compound is selected from the group consisting of:

2-(2-hydroxy-3-isopropylaminopropyl)-5-phenyl-4-isoxazolin-3-one; and pharmaceutically acceptable salts thereof.

30. The method of claim 20, wherein said active compound is selected from the group consisting of:

5-p-chlorophenyl-2-(2-hydroxy-3-isopropylaminopropyl)-4-isoxazolin-3-one; and pharmaceutically acceptable salts thereof.

31. The method of claim 20, wherein said active compound is selected from the group consisting of 2-(2-hydroxy-3-morpholinopropyl)-5-phenyl-4-isoxazolin-3-one and pharmaceutically acceptable salts thereof.

32. The method of claim 17, wherein $R^3$ and R4 together with the intervening nitrogen atom form an alicyclic amino group which is a 5-membered alicyclic amino group, or a 6-membered alicyclic amino group having at least one further heteroatom selected form the group consisting of oxygen heteroatoms, nitrogen heteroatoms and nitrogen heteroatoms substituted with an alkyl group having 1 to 4 carbon atoms.

33. The method of claim 32 wherein said heteroatom is oxygen.

34. The method of claim 32 wherein $R^3$ and $R^4$ together with the intervening nitroatom form

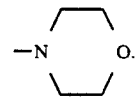

35. The method of claim 34 wherein $R^1$ is hydrogen or halogen and $R^2$ is phenyl or phenyl substituted by $C_1$-$C_4$ alkyl, $C_1$-$C_4$ alkoxy, OH, halogen, $NO_2$ or $CF_3$.

36. The method of claim 35 wherein $R^2$ is phenyl.

37. The method of claim 36 wherein $R^1$ is halogen.
38. The method of claim 32 wherein
$R^1$ is hydrogen or halogen and
$R^2$ is phenyl or phenyl substituted by $C_1$-$C_4$ alkyl, $C_1$-$C_4$ alkoxy, OH, halogen, $NO_2$ or $CF_3$.
39. The method of claim 38 wherein
$R^2$ is phenyl.
40. The method of claim 39 wherein
$R^1$ is halogen.
41. The method of claim 17 wherein
$R^1$ is selected from the group consisting of hydrogen and halogen atoms;
$R^2$ is selected from the group consisting of alkyl groups with 1 to 4 carbon atoms, phenyl groups, phenyl groups substituted with 1 to 3 substituents, or
$R^1$ and $R^2$ together with the intervening carbon atoms form a 6- or 7-membered hydrocarbon ring; and
$R^3$ and $R^4$ together with the intervening nitroatom form

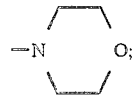

or a pharmaceutically acceptable salt thereof.

* * * * *